United States Patent [19]

Engel et al.

[11] 4,288,437
[45] Sep. 8, 1981

[54] 2-[(AMINO)-ARYL-METHYLENE]-BEN-ZO[B]THIOPHEN-3(2H)-ONES

[75] Inventors: Wolfhard Engel, Biberach; Günter Trummlitz, Warthausen; Ernst Seeger; Joachim Kähling, both of Biberach, all of Fed. Rep. of Germany

[73] Assignee: Boehringer Ingelheim GmbH, Ingelheim am Rhein, Fed. Rep. of Germany

[21] Appl. No.: 173,173

[22] Filed: Jul. 28, 1980

[30] Foreign Application Priority Data

Jul. 31, 1979 [DE] Fed. Rep. of Germany ....... 2931010

[51] Int. Cl.³ .................... A61K 31/38; A61K 31/44; C07D 333/64; C07D 409/06
[52] U.S. Cl. .................................... 424/246; 548/215; 260/244.4; 548/237; 548/240; 260/326.5 SA; 548/300; 260/330; 548/348; 260/330.3; 548/356; 548/379; 424/248.51; 549/54; 549/55; 424/250; 424/251; 424/263; 424/267; 424/270; 424/272; 424/273 R; 424/274; 424/275; 544/3; 544/55; 544/58.2; 544/58.6; 544/58.7; 544/63; 544/96; 544/131; 544/146; 544/238; 544/333; 544/364; 544/376; 546/194; 546/202; 546/274; 548/146; 548/214
[58] Field of Search .......... 260/326.5 SA, 330, 330.3, 260/244.4; 424/246, 248.51, 250, 251, 263, 267, 270, 272, 274, 273 R, 275; 544/3, 55, 58.2, 58.6, 58.7, 63, 96, 131, 146, 238, 333, 364, 376, 367; 546/194, 202, 274; 548/146, 214, 215, 237, 240, 300, 348, 356, 379; 549/55, 54

[56] References Cited

U.S. PATENT DOCUMENTS 2,356,824  8/1944  Cole et al. .................. 549/55 X
3,907,826  9/1975  Stoss et al. .................. 549/55

OTHER PUBLICATIONS

Yugai et al., Chemical Abstracts, vol. 77, (1972) 139873v.

Primary Examiner—Richard Raymond
Attorney, Agent, or Firm—Hammond & Littell, Weissenberger & Muserlian

[57] ABSTRACT

Compounds of the formula

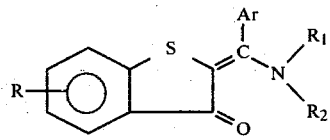

wherein
Ar is phenyl; mono- or di-substituted phenyl, where the substituents are one to two halogens, one to two alkyls of 1 to 3 carbon atoms, or one amino, nitro, cyano or trifluoromethyl; or pyridinyl;
R is hydrogen, chlorine, methyl or methoxy;
$R_1$ is hydrogen or methyl;
$R_2$ is hydrogen, alkyl of 1 to 6 carbon atoms, alkenyl of 2 to 6 carbon atoms, alkynyl of 2 to 6 carbon atoms, cycloalkyl of 3 to 8 carbon atoms, methyl-(cycloalkyl of 3 to 8 carbon atoms) or —A—$R_4$, where A is alkylene of 2 to 3 carbon atoms, and $R_4$ is hydroxyl, methylamino, dimethylamino, N-methyl-ethylamino, diethylamino, pyrrolidino, piperidino, hexamethyleneimino, morpholino or 4-methyl-1-piperazinyl; or
$R_1$ and $R_2$, together with each other and the nitrogen atom to which they are attached, form a 4- to 7-membered, saturated or mono-unsaturated, unsubstituted or substituted heterocycle which may contain nitrogen, oxygen, sulfur, sulfinyl or sulfonyl as additional ring members, where the substituents are alkyls of 1 to 3 carbon atoms.

The compounds are useful as anticonvulsants.

13 Claims, No Drawings

2-[(AMINO)-ARYL-METHYLENE]-BENZO[b]THIOPHEN-3(2H)-ONES

This invention relates to novel 2-[(amino)-arylmethylene]-benzo[b]thiophen-3(2H)-ones, to methods of preparing these compounds, to pharmaceutical compositions containing them as active ingredients, and to methods of using them as anticonvulsants.

More particularly, the present invention relates to a novel class of compounds represented by the formula

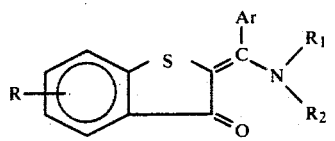

wherein
- Ar is phenyl; mono- or di-substituted phenyl, where the substituents are one to two halogens, one to two alkyls of 1 to 3 carbon atoms, or one amino, nitro, cyano or trifluoromethyl; or pyridinyl;
- R is hydrogen, chlorine, methyl or methoxy;
- $R_1$ is hydrogen or methyl;
- $R_2$ is hydrogen, alkyl of 1 to 6 carbon atoms, alkenyl of 2 to 6 carbon atoms, alkynyl of 2 to 6 carbon atoms, cycloalkyl of 3 to 8 carbon atoms, methyl(cycloalkyl of 3 to 8 carbon atoms) or —A—$R_4$, where A is alkylene of 2 to 3 carbon atoms, and
- $R_4$ is hydroxyl, methylamino, dimethylamino, N-methyl-ethylamino, diethylamino, pyrrolidino, piperidino, hexamethyleneimino, morpholino or 4-methyl-1-piperazinyl; or
- $R_1$ and $R_2$, together with each other and the nitrogen atom to which they are attached, form a 4- to 7-membered, saturated or mono-unsaturated, unsubstituted or substituted heterocycle which may contain nitrogen, oxygen, sulfur, sulfinyl or sulfonyl as additional ring members, where the substituents are alkyls of 1 to 3 carbon atoms, such as pyrrolidino, piperidino, morpholino, N-methylpiperazino, thiomorpholino, thiomorpholino-S-oxide or hexamethyleneimino.

The following are specific examples of compounds which are illustrative of the genus of the formula I.

(E)-2-[(amino)phenylmethylene]-benzo[b]thiophen-3(2H)-one,
(E)-2-[(methylamino)phenylmethylene]-benzo[b]thiophen-3(2H)-one,
(E)-2-[(dimethylamino)phenylmethylene]-benzo[b]thiophen-3(2H)-one,
(E)-2-[(amino)-(2-fluorophenyl)methylene]-benzo[b]thiophen-3(2H)-one,
(E)-2-[(amino)-(2-chlorophenyl)methylene]-benzo[b]thiophen-3(2H)-one,
(E)-2-{[[2-(dimethylamino)ethyl]amino]phenylmethylene}benzo[b]thiophen-3(2H)-one,
(E)-2-{[(2-hydroxyethyl)amino]phenylmethylene}-benzo[b]thiophen-3(2H)-one,
(E)-2-[(amino)-(2-methylphenyl)methylene]-benzo[b]thiophen-3(2H)-one,
(E)-2-[(ethylamino)phenylmethylene]-benzo[b]thiophen-3(2H)-one,
(E)-2-[(amino)-(2-bromophenyl)methylene]-benzo[b]thiophen-3(2H)-one,
(E)-2-[(amino)-(2-iodophenyl)methylene]-benzo[b]thiophen-3(2H)-one,
(E)-2-[(amino)-(3-ethylphenyl)methylene]-benzo[b]thiophen-3(2H)-one,
(E)-2-[(amino)-(2-propylphenyl)methylene]-benzo[b]thiophen-3(2H)-one,
(E)-2-[(amino)-(4-chlorophenyl)methylene]-benzo[b]thiophen-3(2H)-one,
(E)-2-[(amino)-(4-methylphenyl)methylene]-benzo[b]thiophen-3(2H)-one,
(E)-2-[(amino)-(3,4-dichlorophenyl)methylene]-benzo[b]thiophen-3(2H)-one,
(E)-2-[(amino-(4-fluorophenyl)methylene]-benzo[b]thiophen-3(2H)-one,
(E)-2-[(amino)-(4-pyridinyl)methylene]-benzo[b]thiophen-3(2H)-one,
(E)-2-[(amino)-(3-pyridinyl)methylene]-benzo[b]thiophen-3(2H)-one,
(E)-2-[(amino)phenylmethylene]-5-chlorobenzo[b]thiophen-3(2H)-one,
(E)-2-[(amino)phenylmethylene]-6-chlorobenzo[b]thiophen-3(2H)-one,
(E)-2-[(amino)-(2-chlorophenyl)methylene]-5-chlorobenzo[b]thiophen-3(2H)-one,
(E)-2-[(amino)-(2-pyridinyl)methylene]-benzo[b]thiophen-3(2H)-one,
(E)-2-[(amino)-(2-fluorophenyl)methylene]-5-chlorobenzo[b]thiophen-3(2H)-one,
(E)-2-[[(2-propenyl)amino]phenylmethylene]-benzo[b]thiophen-3(2H)-one,
(E)-2-[[[3-(dimethylamino)propyl]amino]phenylmethylene]benzo[b]thiophen-3(2H)-one,
(E)-2-[[[2-(dimethylamino)propyl]amino]phenylmethylene]benzo[b]thiophen-3(2H)-one,
(E)-2-[[[3-(dimethylamino)-2-propyl]amino]phenylmethylene]benzo[b]thiophen-3(2H)-one,
(E)-2-[[[2-(N-methyl-ethylamino)-ethyl]amino]phenylmethylene]benzo[b]thiophen-3(2H)-one,
(E)-2-[[[2-(diethylamino)ethyl]amino]phenylmethylene]-benzo[b]thiophen-3(2H)-one,
(E)-2-[[[2-(1-pyrrolidinyl)ethyl]amino]phenylmethylene]benzo[b]thiophen-3(2H)-one,
(E)-2-[[[2-(1-piperidinyl)ethyl]amino]phenylmethylene]benzo[b]thiophen-3(2H)-one,
(E)-2-[[[2-(hexahydro-1-azepinyl)ethyl]amino]phenylmethylene]benzo[b]thiophen-3(2H)-one,
(E)-2-[[[2-(4-morpholinyl)ethyl]amino]phenylmethylene]benzo[b]thiophen-3(2H)-one,
(E)-2-[(propylamino)phenylmethylene]-benzo[b]thiophen-3(2H)-one,
(E)-2-[(butylamino)phenylmethylene]-benzo[b]thiophen-3(2H)-one,
(E)-2-[[(2-propyl)amino]phenylmethylene]-benzo[b]thiophen-3(2H)-one,
(E)-2-[[(2-methylpropyl)amino]phenylmethylene]-benzo[b]thiophen-3(2H)-one,
(E)-2-[[(1,1-dimethylethyl)amino]phenylmethylene]-benzo[b]thiophen-3(2H)-one,
(E)-2-[[(3-hydroxypropyl)amino]phenylmethylene]-benzo[b]thiophen-3(2H)-one,
(E)-2-[(amino)-(3-methylphenyl)methylene]-benzo[b]thiophen-3(2H)-one,
(E)-2-[(methylamino)-(2-ethyphenyl)methylene]-benzo[b]thiophen-3(2H)-one,
(E)-2-[(ethylamino)-(2-ethylphenyl)methylene]-benzo[b]thiophen-3(2H)-one,
(E)-2-[(amino)-(2-nitrophenyl)methylene]-benzo[b]thiophen-3(2H)-one, (E)-2-[(amino)-(2-aminophenyl)methylene]-benzo[b]thiophen-3(2H)-one,
(E)-2-[(amino)-(2-cyanophenyl)methylene]-benzo[b]thiophen-3(2H)-one,
(E)-2-[(amino)phenylmethylene]-6-methylbenzo[b]thiophen-3(2H)-one,
(E)-2-[(amino)phenylmethylene]-5-methylbenzo[b]thiophen-3(2H)-one and
(E)-2-[(amino)phenylmethylene]-6-methoxybenzo[b]thiophen-3(2H)-one.

A preferred sub-genus is constituted by those compounds of the formula I
wherein
Ar is unsubstituted or o-substituted phenyl, where the substituent is fluorine, chlorine, bromine, methyl or ethyl;
R is hydrogen;
$R_1$ is hydrogen or methyl; and
$R_2$ is hydrogen, methyl, ethyl, β-hydroxy-ethyl or β-dimethylamino-ethyl.

The compounds embraced by formula I may be prepared by the following methods:

Method A

By reacting a 2-acyl-benzo[b]thiophen-3-ol of the formula

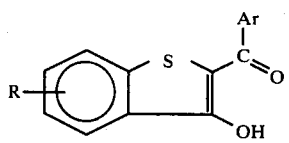

(II)

wherein Ar and R have the meanings previously defined, or an enol ether of the formula

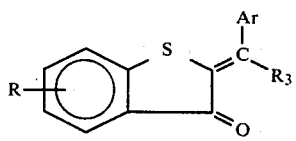

(III)

wherein
Ar and R have the meanings previously defined, and
$R_3$ is alkyl, alkenyl or phenylalkyl of up to 20 carbon atoms, where the phenyl moiety may be halo-, nitro- or methyl-substituted,
with an amine of the formula

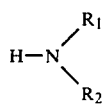

(IV), an ammonium salt of the formula $H_2N^{\oplus}R_1R_2B^{\ominus}$ 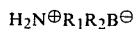 (IVa)

or a urea of the formula

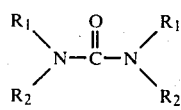

(V)

where $R_1$ and $R_2$ have the meanings previously defined, and
B is the anion of a monobasic or polybasic, weak to moderately strong organic or inorganic acid, such as boric acid, formic acid, acetic acid, propionic acid, n-butyric acid, benzoic acid, nicotinic acid, carbonic acid, carbamic acid, oxalic acid, succinic acid, citric acid, thiocyanic acid and phosphoric acid.

The reaction is performed in an excess of the particular amine of the formula IV or in a polar protic or aprotic solvent, such as in methanol, ethanol, 2-propanol, tetrahydrofuran, dioxane, dimethylformamide, dimethylacetamide, dimethylsulfoxide, hexamethylphosphoric triamide, pyridine, formic acid, acetic acid, propionic acid or isobutyric acid, at temperatures between −20° and 160° C., preferably between 110° and 130° C., and optionally at elevated pressure in an autoclave. The compounds of the formulas IV, IVa or V are generally used in an excess of 3 to 10 mols, based on the compound of general formula II or III to be reacted. However, it is also possible to use equimolar quantities of the reactants.

Method B

For the preparation of a compound of the formula I wherein $R_1$ and $R_2$ are hydrogen, by reacting a 2-acyl-benzo[b]thiophen-3-ol of the formula II or an enol ether of the formula III with formamide, or by reacting a 2-acyl-3-chloro-benzo[b]thiophen of the formula

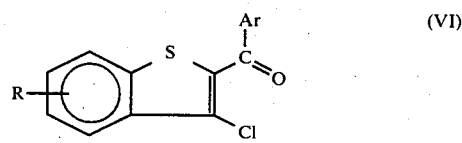

(VI)

wherein R and Ar have the meanings previously defined, with an ammonium salt of the formula $NH_4^{\oplus}B^{\ominus}$  (VIb)

wherein B has the meanings previously defined.

The reaction is carried out in a polar, protic or aprotic solvent, such as in methanol, ethanol, 2-propanol, tetrahydrofuran, dioxane, dimethylformamide, dimethylacetamide, pyridine, dimethylsulfoxide or hexamethylphosphoric triamide, but preferably in a lower aliphatic carboxylic acid such as formic, acetic, propionic or n-butyric acid, at temperatures between 20° and 160° C., preferably between 110° and 130° C., and optionally at elevated pressure in an autoclave. The use of an excess of formamide or of the ammonium salt of the formula (VIb) of up to 10 mols is advantageous with regard to the yield of the compound of the formula I, but it is also possible to use equimolar amounts of the reactants VI and VIb or formamide.

Method C

By reacting a 2-acyl-benzo[b]thiophen-3-ol of the formula II with phosphorus (V)chloride, followed by aminolysis of the resulting unstable salt of the assumed but unconfirmed formula

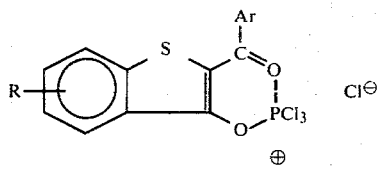

(VII)

wherein Ar and R have the meanings previously defined, with an amine of the formula IV. In addition to the desired end product of the formula I, the aminolysis yields a non-stoichiometric phosphorus-containing intermediate of the suspected but also unconfirmed formula

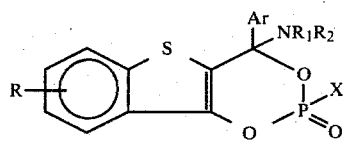

(VIII)

wherein

Ar, R, $R_1$ and $R_2$ have the meanings previously defined, and

X is chlorine, hydroxyl or —$NR_1R_2$, where $R_1$ and $R_2$ have the meanings previously defined, or a random mixture of these radicals.

Hydrolysis of the intermediate with a dilute mineral acid also yields the desired end product of the formula I in the form of the corresponding mineral acid salt.

The reaction of the 2-acyl-benzo[b]thiophen-3-ol of the formula II with phosphorus(V)chloride is carried out in an inert, hydrocarbon-like solvent, such as petroleum ether, petrol, benzene, toluene, xylene, chlorobenzene or 1,2-dichlorobenzene, and at temperatures between 0° and 40° C., preferably between 15° and 25° C. In view of their instability, it is advantageous to quickly further react the salt of the assumed structure VII with an amine of the formula IV. The amine of the formula IV is preferably used in the form of an aqueous solution, but can also be used as such. An excess of 2 to 20 mols of the amine of the formula IV is used per mol of the salt complex of the formula VII. However, equimolar amounts of the amine of the formula IV suffice when additional bases, such as sodium carbonate, potassium carbonate, sodium bicarbonate, potassium bicarbonate or tert. amines such as triethylamine, trimethylamine, 1,5-diazabicyclo[4,3,0]non-5-ene or 1,8-diazabicyclo[5,4,0]undec-7-ene are added. The aminolysis, which is generally performed as a two-phase reaction, is carried out at temperatures between 0° and 100° C., preferably between 40° and 60° C.

The nitrogen- and phosphorus-containing compound of the assumed formula VIII can be converted into the corresponding salt of the desired end product of the formula I by treatment with a dilute, aqueous mineral acid. Examples of suitable aqueous mineral acids are 1 to 20% aqueous hydrochloric acid, hydrobromic acid or hydroiodic acid, as well as 1 to 50% aqueous sulfuric or phosphoric acid. Temperatures between 30° and 100° C., preferably between 50° and 70° C. are suitable for the hydrolysis reaction. The salt obtained can be converted into the desired end product of the formula I in a conventional manner by treatment with a base, such as an aqueous solution of sodium hydroxide, potassium hydroxide, calcium hydroxide, potassium carbonate, sodium carbonate, sodium bicarbonate, ammonia or an amine such as methylamine or triethylamine.

Method D

For the preparation of a compound of the formula I wherein $R_1$ and $R_2$ are hydrogen, by reducing a compound of the formula

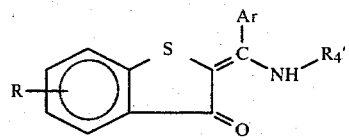

(IX)

wherein

Ar and R have the meanings previously defined, and $R_4'$ is hydroxyl or —$NR_5R_6$, where $R_5$ and $R_6$, which may be identical to or different from each other, are each alkyl of 1 to 6 carbon atoms, or $R_5$ is hydrogen and $R_6$ is phenyl optionally substituted by halogen, alkyl of 1 to 3 carbon atoms or alkoxy of 1 to 3 carbon atoms.

The following reduction methods may be used:

(a) Hydrogenation in the presence of a catalytically activated metal of the 8th subgroup of the Periodic Table of Elements. Palladium and platinum catalysts, for example palladium on animal charcoal or finely divided platinum formed in situ from platinum(IV) oxide, are particularly suitable. The hydrogenation is preferably performed in a polar solvent, such as glacial acetic acid, propionic acid, methanol, ethanol, dioxane or tetrahydrofuran, and optionally in the presence of a strong mineral acid, such as perchloric, sulfuric or orthophosphoric acids, at temperatures between 0° and 50° C., but preferably at room temperature and at a hydrogen pressure of 0.5 to 5 bar. However, it is also possible to use a higher hydrogen pressure. If Ar in a compound of the formula IX is nitrophenyl, the nitro group is also reduced to an amino group.

(b) Reduction by means of nascent nitrogen and/or tin(II) chloride. Reduction by means of iron powder in the presence of a dilute or semi-concentrated mineral acid such as hydrochloric, hydrobromic, sulfuric or phosphoric acid, and reduction by means of tin(II) chloride in the presence of concentrated hydrochloric or hydrobromic acid have proved to be particularly suitable. When reducing by means of iron, the preferred solvent is a polar, water-miscible organic solvent such as methanol, ethanol, dioxane, tetrahydrofuran or glacial acetic acid. The working temperature is between 10° and 100° C., preference being given to room temperature. For the tin(II) chloride method, temperatures between 0° and 40° C., but preferably room temperature are used, and the aforementioned solvents are additionally employed. If Ar in a compound of the formula IX is nitrophenyl, the nitro group is also reduced.

(c) Reduction with a complex alkali metal aluminum hydride, preferably lithium aluminum hydride or sodium bis-(2-methoxyethoxy)-aluminum hydride, using an anhydrous ether, such as diethyl ether, dioxane, tetrahydrofuran, 1,2-dimethoxyethane, diethylene glycol dimethyl ether or triethylene glycol dimethyl ether, as the solvents, at temperatures between −20° and 100° C. preferably between +20° and +50° C. If Ar in a compound of the formula IX is nitrophenyl, the nitro group is also reduced to an amino group.

(d) Reduction with sodium dithionite in aqueous solution or suspension in the presence of excess alkali metal hydroxide. The reaction may be performed with or without an additional solvent, such as methanol, ethanol, dioxane, tetrahydrofuran, 1,2-ethane-diol, 1,2-dimethoxy-ethane or 2-ethoxy-ethanol. The reaction temperature can be from 60° to 120° C., but the boiling point of water is preferred. If Ar in a compound of the formula IX is nitrophenyl, the nitro group is also reduced to an amino group.

(e) Reduction with iron(II) hydroxide in aqueous solution or suspension at temperatures between 0° and 100° C., preferably between 15° and 50° C. The reaction can be performed with or without an additional solvent, such as methanol, ethanol, dioxane, tetrahydrofuran, 1,2-ethanediol, 1,2-dimethoxy-ethane or 2-ethoxyethanol. Iron (II) hydroxide is preferably formed in situ from suitable iron(II) salts, such as from iron(II) sulfate heptahydrate, iron (II) chloride, iron(II) chloride tetrahydrate or iron(II) nitrate hexahydrate by adding a base, preferably an aqueous ammonia solution. If Ar in a compound of the formula IX is nitrophenyl, the nitro group is also reduced to an amino group.

Method E

For the preparation of a compound of the formula I wherein $R_1$ is hydrogen, and $R_2$ is hydrogen; alkyl, alkenyl or alkynyl of up to 6 carbon atoms; cycloalkyl of 3 to 8 carbon atoms optionally substituted by methyl; or —A—$R_4$, where A and $R_4$ have the meanings previously defined:

By reacting a compound of the formula

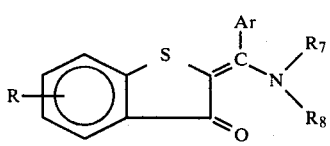

wherein $R_7$ is hydrogen or methyl, and $R_8$ is hydrogen; alkyl, alkenyl or alkynyl of up to 6 carbon atoms; cycloalkyl of 3 to 8 carbon atoms optionally substituted by methyl; or —A—$R_4$, where Ar, R, A and $R_4$ have the meanings previously defined, with an amine of the formula IV, with an ammonium salt of the formula IVa or with a urea of the formula V.

The reaction is performed in an excess of the particular amine of the formula V or in a polar, protic or aprotic solvent, such as in methanol, ethanol, 2-propanol, tetrahydrofuran, dioxane, dimethylformamide, dimethylacetamide, dimethylsulfoxide, hexamethylphosphoric triamide, pyridine, formic acid, acetic acid, propionic acid or isobutyric acid, at temperatures between −20° and 160° C., preferably between 110° and 130° C., and optionally at elevated pressure in an autoclave. The compounds of the formulas IV, IVa and V are generally used in an excess of 2 to 10 mols, based on the substrate of the formula X to be reacted, but it is also possible to use equimolar amounts of the reactants.

The starting compounds of the formula II are either described in the literature or can be prepared in accordance with processes described in the literature (K. Görlitzer, Arch.Pharm. 307, 523 [1974]). For example, the following 2-acyl-benzo[b]thiophen-3-ols were obtained from the corresponding methyl thiosalicylates optionally substituted in the benzene ring and appropriate 2-chloro- or 2-bromo-1-aryl-ethanones.

2-(4-chlorobenzoyl)-benzo[b]thiophen-3-ol, m.p. 124°–125° C. (petroleum ether/ethyl acetate 1:1);

2-(4-methylbenzoyl)-benzo[b]thiophen-3-ol, m.p. 100°–101° C. (petroleum ether/ethyl acetate 1:1);

2-(3,4-dichlorobenzoyl)-benzo[b]thiophen-3-ol, m.p. 176°–178° C. (ethyl acetate);

2-(4-fluorobenzoyl)-benzo[b]thiophen-3-ol, m.p. 118°–120° C. (ethyl acetate);

(3-hydroxy-benzo[b]thien-2-yl)-4-pyridinyl-methanone, m.p. 139°–140° C. (methanol);

2-benzoyl-5-chlorobenzo[b]thiophen-3-ol, m.p. 129°–132° C. (methanol);

2-benzoyl-6-chlorobenzo[b]thiophen-3-ol, m.p. 160°–162° C. (methanol/ethyl acetate 1:1);

2-(2-fluorobenzoyl)-benzo[b]thiophen-3-ol, m.p. 99°–100° C. (petroleum ether/ethyl acetate 1:1);

2-(2-chlorobenzoyl)-benzo[b]thiophen-3-ol, m.p. 86°–88° C. (methanol);

(3-hydroxy-benzo[b]thiene-2-yl)-2-pyridinyl-methanone, m.p. 167°–168° C. (ethyl acetate);

2-(2-chlorobenzoyl)-5-chlorobenzo[b]thiophen-3-ol, m.p. 136°–138° C. (ethyl acetate/methanol 1:1);

2-(2-methylbenzoyl)-benzo[b]thiophen-3-ol, m.p. 126°–127° C. (ethyl acetate/methanol 1:1);

2-(3-methylbenzoyl)-benzo[b]thiophen-3-ol, m.p. 89°–92° C. (petroleum ether/ethyl acetate 1:1);

2-(2-ethylbenzoyl)-benzo[b]thiophen-3-ol, m.p. 39°–40° C. (methanol);

2-(2-nitrobenzoyl)-benzo[b]thiophen-3-ol, m.p. 151°–153° C. (ethyl acetate);

2-(2-bromobenzoyl)-benzo[b]thiophen-3-ol, m.p. 108°–110° C. (methanol);

2-(2-trifluoromethyl-benzoyl)-benzo[b]thiophen-3-ol, m.p. 91°–92° C. (methanol);

2-benzoyl-5-methylbenzo[b]thiophen-3-ol, m.p. 109°–111° C. (methanol/ethyl acetate 1:1);

2-(2-aminobenzoyl)-benzo[b]thiophen-3-ol, m.p. 129°–131° C. (ethyl acetate);

2-benzoyl-6-methylbenzo[b]thiophen-3-ol, m.p. 100°–102° C. (methanol/ethylacetate 1:1);

2-benzoyl-6-methoxybenzo[b]thiophen-3-ol, m.p. 138°–139° C. (methanol);

2-benzoyl-4-methylbenzo[b]thiophen-3-ol, m.p. 122°–123° C. (methanol/ethyl acetate 1:1).

The starting compounds of the formula III, which are new, are obtained according to method C above by using, in place of an amine of the formula IV, a mixture of an alcohol of the formula $R_3$—OH and a tertiary amine, preferably triethylamine. In this way, for example, the following compound was prepared:

(E)-2-[(methoxy)phenylmethylene]-benzo[b]thiophen-3(2H)-one, m.p. 136°–138° C. (diisopropyl ether/petroleum ether 1:1)

$C_{16}H_{12}O_2S$ (268.33): Calc.: C-71.62%; H-4.51%; S-11.95%; Found: C-71.46%; H-4.83%; S-11.98%.

IR($CH_2Cl_2$):2845 ($OCH_3$), C=O 1670 cm$^{-1}$

UV (ethanol); λmax (neutral) 255 (E=0.74), 299 (E=0.68), 414 (E=0.25) nm; λmax (alkaline) 257 (E=0.69), 300 (E=0.42), 413 (E=0.15) nm Concentration: 50 μg/ml; layer thickness 0.2 cm, 1H-NMR (CDCl$_3$; 80 MHz): δ8.2–7.0 (9H-m; ar.H); 3.69 (3H-s; —O—CH$_3$);

MS: m/e 268(s), 254, 239, 237, 197, 176(s) 165, 126.5, 121, 105, 77(s), 51, 28(s).

The starting compounds of the formulas IV and V are known from the literature and are, in general, commercially available. The starting compounds of the formulas IVa and IVb can easily be prepared by reacting a corresponding amine of the formula IV with an appropriate acid.

The starting compounds of the formula VI are known from the literature (T. Higa and A. J. Krubsack, J. Org. Chemistry 41, 3399 [1976]) or are obtained from the unstable salts of the formula VII after prolonged storage at room temperature or after gentle heating to temperatures between 30° and 80° C. Thus, for example, the following compound was obtained:

2-Benzoyl-3-chlorobenzo[b]thiophene, m.p. 71°–73° C. (cyclohexane).

The starting compounds of the formula IX are either known (S. B. Arwad and N. F. Abdul-Malik, Austr. J. Chem. 28, 601-5 [1975]) or can be prepared from the compounds of the formula II according to method C above by replacing the amines of the formula IV with compounds of the formula $H_2NR'_4$; or, where $R'_4$ is hydroxyl, they can easily be obtained from compounds of the formula II by boiling with hydroxylamine hydrochloride in a mixture of pyridine and ethanol. In this way, for example, the following compounds may be prepared:

(E)-2-[(2-phenylhydrazino)phenylmethylene]benzo[b]thiophen-3(2H)-one, m.p. 168° C. (methanol/acetone 1:1);

(E)-2-[(hydroxyamino)phenylmethylene]-benzo[b]thiophen-3-(2H)-one, m.p. 128°–130° C. (petroleum ether/ethyl acetate 1:1);

$C_{15}H_{11}NO_2S$ (269.32): Calc.: C-66.90%; H-4.12%; N-5.20%; S-11.90%; Found: C-66.90%; H-4.06%; N-5.14%; S-12.06%.

IR ($CH_2Cl_2$): OH 3550; associated n-H, O—H 3400 to 2500; C=O 1595 C=C 1610, 1570 $cm^{-1}$ UV (ethanol): λmax (neutral) 257 (E=0.70); 304–316 (E=0.34); 330 (E=0.32) nm; λmax (alkaline) 220 (E=0.86); 275 (E=0.47); 405 (E=0.33) nm;

(Concentration: 50 μg/ml; layer thickness 0.2 cm).

The starting compounds of the formula X can be prepared analogously.

The following examples illustrate the present invention and will enable others skilled in the art to understand it more completely. It should be understood, however, that the invention is not limited solely to the particular examples given below.

EXAMPLE 1

(E)-2-[(Amino)phenylmethylene]-benzo[b]thiophen-3(2H)-one 50.86 gm (0.2 mol) of 2-benzoyl-benzo[b]thiophen-3-ol were dissolved in 600 cc of toluene in a 1-liter separating funnel and after adding 42.0 gm (0.2 mol) of phosphorus(V) chloride the solution was mechanically stirred for five minutes at room temperature. The suspension of the resulting red complex is subsequently introduced, while vigorously stirring, into 150 cc (about 2 mols) of concentrated ammonia, the reaction temperature being maintained at 40° to 50° C. by external cooling with water. Heating at 50° C. was continued for one hour, followed by cooling, addition of hydrochloric acid to give a pH of 1 and refluxing until the yellow starting spot could no longer be detected by thin-layer chromatography (silica gel pre-prepared thin-layer chromatography plates $F_{254}$ Merck; 1,2-dichloroethane/ethyl acetate/glacial acetic acid 100:30:3). This was followed by cooling to +10° C., filtering with suction after standing for one hour at this temperature, and washing of the precipitate with a little toluene and then thoroughly with water to remove inorganic salts.

The orange toluene phase was separated from the combined filtrates, washed once with 500 cc of water and concentrated by evaporation. The resulting, partly crystalline residue was boiled twice with 20 cc each of methanol, and the solutions were each cooled to +10° C. (E)-2-[(amino)phenylmethylene]-benzo[b]thiophen-3(2H)-one hydrochloride went into solution, while the unreacted starting substance remained undissolved.

The methanol solutions obtained were combined with the solution of the above-obtained crystalline precipitate in 25 cc of methanol, admixed with 25 cc of ammonia and subsequently the desired product was precipitated in the form of yellow crystals.

This was followed with suction, drying of the precipitate in a vacuum drier, dissolving the product in 70 cc of ethyl acetate, addition of just enough petroleum ether to ensure that no precipitate formed (about 40 cc), addition of 40 gm of activated charcoal, boiling and filtering while hot. By adding 100 cc of petroleum ether and cooling to +10° C., the pure end product was obtained from the cooled filtrate. After standing for two hours and then filtering with suction, the precipitate was thoroughly washed with approximately 40 cc of petroleum ether. After concentrating the combined mother liquors to about 50 cc total volume, additional end product with the same quality was obtained. After drying in vacuo, the yellow crystals melted at 121.6°–122.5° C.

Yield: 35.6 gm (70% of theory).

TLC-proof:

Stationary phase: silica gel pre-prepared thin-layer chromatography plates ($F_{254}$Merck)

Mobile phase: (a) 1,2-dichloroethane: $R_F$ starting material 0.7; $R_F$ product 0.15; (b) 1,2-dichloroethane/ethyl acetate/glacial acetic acid (100:30:3): $R_F$ starting material 0.9; $R_F$ product 0.4

$C_{15}H_{11}NOS$ (253.32): Calc.: C-71.12%; H-4.38%; N-5.53%; S-12.66%; Found: C-71.20%; H-4.59%; N-5.59% S-12.52%.

IR(KBr): N—H 3475, C=O 1600 $cm^{-1}$

UV(ethanol): λmax 184, 317, 430 nm, shoulder at 270 nm $^1$H-NMR(CDCl$_3$): δ11.0 (1H, wide, internal H bridge); 8.01 (1H-dd, J=7.6 and 2 Hz, ar.H); 7.9–7.1 (8H-m, ar.H); 5.78 (1H-s, exchangeable H)

$^{13}$C-NMR(CDCl$_3$); 22.63 MHz): δ103.66; 185.55 (C=O); 131.28; 123.48; 131.80; 124.20; 144.80; 136.87; 160.07; 134.53; 127.97; 129.40; 125.82.

In the same way as above was obtained, the $^{15}$N-labeled compound, in which the signal for the carbon adjacent to $^{15}$N splits:

δ160.59 (d, J$^{15}$N-C 14.71 Hz).

EXAMPLE 2

(E)-2-[(Methylamino)phenylmethylene]-benzo[b]thiophen-3-(2H)-one

Prepared in the same way as in Example 1 from 2-benzoyl-benzo[b]thiophen-3-ol, phosphorus (V) chloride and 40% aqueous methylamine solution with a yield of 43% of theory.

M.p. 155°–156° C. (methanol)

$C_{16}H_{13}NOS$ (267.34): Calc.: C-71.88% H-4.90%; N-5.24%; S-11.99%; Found: C-72.10%; H-4.75%; N-5.21%; S-12.20%.

EXAMPLE 3

(E)-2-[(Amino)-(4-chlorophenyl)methylene]-benzo[b]thiophen-3(2H)-one

Prepared as in Example 1 from 2-(4-chlorobenzoyl)-benzo[b]thiophen-3-ol, phosphorus(V) chloride and concentrated aqueous ammonia with a yield of 55% of theory.

Mp. 182°–183° C. (benzene)

$C_{15}H_{10}ClNOS$ (287.77) Calc.: C-62.61%; H-3.50%; Cl-12.32%; N-4.87%; S-11.14%; Found: C-62.90%; H-3.62%; Cl-12.55%; N-4.76%; S-11.18%.

EXAMPLE 4

(E)-2-[(Dimethylamino)phenylmethylene]-benzo[b]thiophen-3(2H)-one

Prepared as in Example 1 from 2-benzoyl-benzo[b]thiophen-3-ol, phosphorus(V) chloride and 40% aqueous dimethylamine solution with a yield of 7% of theory.

M.p. 178°–180° C. (ethyl acetate/petroleum ether 1:1)

$C_{17}H_{15}NOS$ (281.38) Calc.: C-72.57%; H-5.37%; N-4.98%; S-11.39%; Found: C-72.17%; H-5.33%; N-4.80%; S-11.37%.

IR($CH_2Cl_2$): C=O 1610 $cm^{-1}$

UV (ethanol): λmax 270 to 290 (E=0.43), 332 (E=0.42) and 454 (E=0.37) nm (layer thickness 0.2 cm; concentration 50 μg/ml)

$^1$H-NMR ($CDCl_3$; 80 MHz): δ7.99 (1H-dd, I=7 and 2 Hz; ar.H); 7.7–7.2 (8H-m ar.H); 3.28 (6H-s).

EXAMPLE 5

(E)-2-[(Amino)-(4-methylphenyl)methylene]-benzo[b]thiophen-3(2H)-one

Prepared as in Example 1 from 2-(4-methylbenzoyl)-benzo[b]thiophen-3-ol, phosphorus(V) chloride and concentrated ammonia with a yield of 62% theory.

M.P. 147° C. (ethyl acetate/petroleum ether 1:1)

$C_{16}H_{13}NOS$ (267.34): Calc.: C-71.88%; H-4.90%; N-5.24%; S-11.99%; Found: C-71.38%; H-4.82%; N-5.14%; S-12.58%.

EXAMPLE 6

(E)-2-[(Amino)-(3,4-dichlorophenyl)methylene]-benzo[b]thiophen-3(2H)-one

Prepared as in Example 1 from 2-(3,4-dichlorobenzoyl)-benzo[b]thiophen-3-ol, phosphorus(V) chloride and concentrated ammonia with a yield of 50% of theory.

M.p. 169°–170° C. (ethyl acetate)

$C_{15}H_9Cl_2NOS$ (322.21): Calc.: C-55.92%; H-2.82%; Cl-22.01%; N-4.35%; S-9.95%; Found: C-55.81%; H-3.06%; Cl-22.45%; N-4.47%; S-10.10%.

EXAMPLE 7

(E)-2-[(Amino)-(4-fluorophenyl)methylene]-benzo[b]thiophen-3(2H)-one

Prepared as in Example 1 from 2-(4-fluorobenzoyl)-benzo[b]thiophen-3-ol, phosphorus(V) chloride and concentrated ammonia with a yield of 63% of theory. Yellow, felt-like crystals; M.p. 158° C. (methanol).

$C_{15}H_{10}FNOS$ (271.31): Calc. C-66.41%; H-3.72%; N-5.16%; S-11.82%; Found: C-66.51%; H-4.00%; N-5.23%; S-11.92%

IR($CH_2Cl_2$): N—H 3465, C=O 1610 $cm^{-1}$

UV (ethanol): λmax 282, 315, 428 nm; shoulder at 260 nm $^1$H-NMR ($CDCl_3$): δ 11.07 (1H, wide, internal H-bridge); 8.08 (1H-dd, J=7.5 and 2 Hz; ar. H); 7.95–7.1 (7H-m; ar.H); 5.86 (1H, broad, exchangeable H).

EXAMPLE 8

(E)-2-[(Amino)-(4-pyridinyl)methylene]-benzo[b]thiophen-3(2H)-one

Prepared as in Example 1 from (3-hydroxy-benzo[b]-thien-2-yl)-4-pyridinyl-methanone, phosphorus(V) chloride and aqueous 25% ammonia solution with a yield of 6% of theory.

M.p. 198°–200° C. (methanol)

$C_{14}H_{10}N_2OS$ (254.30): Calc.: C-66.12%; H-3.96%; N-11.02%; S-12.61%; Found: C-65.99%; H-3.92%; N-10.80%; S-12.30%

IR(KBr): N—H broad 3470 to 2800; C=O 1620 $cm^{-1}$

UV (ethanol): λmax 275–281 (E=0.50), 310 (E=0.45), 431 (E=0.43) nm; after adding alkali: λmax 285 (E=0.80), 395 (E=0.33) nm (Concentration: 50 μg/ml; layer thickness 0.2 cm)

$^1$H-NMR ($CDCl_3/CD_3OD$); 80 MHz): δ 8.86 (2H-dd, J=5 Hz and 2 Hz; α-pyridyl-H); 8.07 (1H-dd, J=7 and 2 Hz; ar. H); 7.85–7.2 (5H-m; ar.H); 2 exchangeable hydrogen atoms.

EXAMPLE 9

(E)-2-[(Amino)phenylmethylene]-5-chloro-benzo[b]thiophen-3(2H)-one

Prepared as in Example 1 from 2-benzoyl-5-chloro-benzo[b]-thiophen-3-ol, phosphorus(V) chloride and concentrated ammonia with a yield of 57% of theory.

M.p. 172°–173° C. (ethyl acetate)

$C_{15}H_{10}ClNOS$ (287.77): Calc.: C-62.61%; H-3.50%; Cl-12.32%; N-4.87%; S-11.14%; Found: C-62.39%; H-3.47%; Cl-12.31%; N-4.77%; S-11.45%

IR(KBr): N-H (or O—H) 3450, 3330, 3140; C=O 1625 $cm^{-1}$

UV (ethanol): λmax 258 (E=0.42), 287 (E=0.53), 322 (E=0.48), λ4.34 (E=0.49) nm; after adding alkali: λmax 286 (E=0.62); 320 shoulder (E=0.23); 393 (E=0.30); 434 shoulder. (Concentration: 50 μg/ml; layer thickness 0.2 cm)

EXAMPLE 10

(E)-2-[(Amino)phenylmethylene]-6-chlorobenzo[b]thiophen-3(2H)-one

Prepared as in Example 1 from 2-benzoyl-6-chlorobenzo[b]-thiophen-3-ol, phosphorus(V) chloride and concentrated ammonia with a yield of 27% theory.

M.p. 191°–192° C. (ethyl acetate).

$C_{15}H_{10}ClNOS$ (287.77) Calc.: C-62.61%; H-3.50%; Cl-12.32%; N-4.87%; S-11.14%; Found: C-62.80%; H-3.50%; Cl-12.40%; N-5.11%; S-11.08%

IR(KBr): N-H 3470 and broad bands at 3220 and 3120; C=O 1600 $cm^{-1}$

UV (ethanol): λ max (neutral) 286 (E=0.64), 309 (E=0.54), 425 (E=0.55) nm; λ max (alkaline) 284(E=0.67), 308 shoulder (E=0.33), 405 (E=0.33), 428 (shoulder) nm.

(Concentration: 50 μg/ml; layer thickness: 0.2 cm).

EXAMPLE 11

(E)-2-[(Amino)-(2-fluorophenyl)methylene]-benzo[b]thiophen-3(2H)-one

Prepared as in Example 1 from 2-(2-fluorobenzoyl)-benzo[b]-thiophen-3-ol, phosphorus(V) chloride and concentrated ammonia, but using a mixture of toluene and petroleum ether in a volume ratio of 2:1 in place of pure toluene, giving a yield of 50% of theory. Yellow crystals; m.p. 156°-158° C. (ethyl acetate/petroleum ether 1:1).

$C_{15}H_{10}FNOS$ (271.31): Calc.: C-66.41%; H-3.72%; N-5.16%; S-11.82%; Found: C-66.11%; H-3.61%; N-5.25%; S-12.57%.

IR(KBr): N—H 3475, as well as associated N-H; C=O 1600 cm$^{-1}$

UV (ethanol): λ max (neutral) 258 (shoulder), 281, 312, 424 nm; λ max (alkaline) 281, 310 (shoulder), 388, 422 (shoulder) nm.

EXAMPLE 12

(E)-2-[(Amino)-(2-chlorophenyl)methylene]-benzo[b]thiophen-3(2H)-one

Prepared as in Example 1 from 2-(2-chlorobenzoyl)-benzo[b]-thiophen-3-ol, phosphorus(V) chloride and concentrated ammonia with a yield of 33% of theory; m.p. 167°-168° C. (ethyl acetate)

$C_{15}H_{10}ClNOS$ (287.77): Calc.: C-62.61%; H-3.50%; Cl-12.32%; N-4.87%; S-11.14%; Found: C-63.10%; H-3.70%; Cl-12.95%; N-4.84%; S-11.78%

IR(KBr): N—H 3470 (as well as associated N-H); C=O 1600 cm$^{-1}$

UV (ethanol): λ max (neutral) 260 shoulder (E=0.41); 283 (E=0.51); 310 (E=0.49); 422 (E=0.46) nm; λ max (alkaline) 283 (E=0.60); 308 shoulder (E=0.11); 380-385 (E=0.32) nm;

(Concentration: 50 μg/ml; layer thickness: 0.2 cm).

EXAMPLE 13

(E)-2-[(Amino)-(2-pyridinyl)methylene]-benzo[b]thiophen-3-(2H)-one

Prepared as in Example 1 from (3-hydroxybenzo[b]thien-2-yl)-2-pyridinyl-methanone, phosphorus(V) chloride and concentrated ammonia with a yield of 27% of theory. M.p. 128°-130° C. (ethyl acetate) $C_{14}H_{10}N_2OS$ (254.30): Calc.: C-66.12%; H-3.96%; N-11.02%; S-12.61%; Found: C-66.34%; H-4.09%; N-11.45%; S-12.70%.

IR(KBr): N—H or associated N—H 3290; C=O approx. 1600 cm$^{-1}$

UV (ethanol): λ max (neutral) 250 shoulder (E=0.39); 274 (E=0.58); 329 (E=0.49) and >390 nm; λ max (alkaline) 286 (E=0.65); 325 shoulder (E=0.30); >390 nm;

(Concentration: 50 μg/ml; layer thickness 0.2 cm).

EXAMPLE 14

(E)-2-[(Amino)-(2-chlorophenyl)methylene]-5-chlorobenzo[b]-thiophen-3(2H)-one

Prepared as in Example 1 from 2-(2-chlorobenzoyl)-5-chlorobenzo[b]thiophen-3-ol, phosphorus(V) chloride and concentrated aqueous ammonia with a yield of 40% of theory; m.p. 199°-201° C. (ethyl acetate).

$C_{15}H_9Cl_2NOS$ (322.21): Calc.: C-55.92%; H-2.82%; Cl-22.01%; N-4.35%; S-9.95%; Found: C-55.67%; H-3.09%; Cl-21.70%; N-4.22%; S-10.30%.

IR(CH$_2$Cl$_2$): N—H 3475 (as well as associated N—H) C=O 1610 cm$^{-1}$

UV (ethanol): λmax (neutral) 260 (E=0.34); 293 (E=0.52); 314 (E=0.44); 432 (E=0.44) nm; λmax (alkaline) 293 (E=0.64); 320 shoulder (E=0.16); 390 (E=0.32) nm (Concentration: 50 μg/ml; layer thickness: 0.2 cm).

EXAMPLE 15

(E)-2-{[(2-Propenyl)amino]phenylmethylene}-benzo[b]thiophen-3(2H)-one

Prepared as in Example 1 from 2-benzoyl-benzo[b]thiophen-3-ol, phosphorus(V) chloride and a solution of one part by volume of allylamine in 2 parts by volume of water with a yield of 43% of theory. M.p. 104°-106° C. (ethyl acetate).

$C_{18}H_{15}NOS$ (293.39): Calc.: C-73.69%; H-5.15%; N-4.77%; S-10.93%; Found: C-73.48%; H-5.22%; N-4.78%; S-11.18%.

IR(CH$_2$Cl$_2$): C=C 1645, C=O approx. 1600 cm$^{-1}$

UV (ethanol): λ max (neutral) 265 shoulder E=0.42); 286 (E=0.52); 320 (E=0.56); 431 (E=0.60).

No change upon adding alkali (Concentration 50 μg/ml; layer thickness 0.2 vm)

$^1$H—NMR(CDCl$_3$): δ12.0 (1H, broad, internal H-bridge); 8.05 (1H-dd), J=7 and 2 Hz ar.H); 7.7-7.15 (8H-m; ar.H); 6.15-5.6 (1H-m); olefinic H); 5.45-5.05 (2H-m; olefin. H); 4.0-3.7 (2H-m aliph. CH$_2$).

EXAMPLE 16

(E)-2-{[[2-(Dimethylamino)ethyl]amino]phenylmethylene}benzo-[b]thiophen-3(2H)-one Prepared as in Example 1 from 2-benzoyl-benzo[b]thiophen-3-ol, phosphorus(V) chloride and a solution of 2 parts by volume of N,N-dimethyl-ethylenediamine in 3 parts by volume of water with a yield of 42% of theory. Orange yellow crystals; m.p. 123°-125° C. (ethyl acetate).

$C_{19}H_{20}N_2OS$ (324.44): Calc.: C-70.34%; H-6.21%; N-8.63%; S-9.88%; Found: C-70.16%; H-6.11%; N-8.65%; S-10.17%.

IR(CH$_2$Cl$_2$): NH associated; C=O 1600 cm$^{-1}$

UV (ethanol): λ max (neutral) 287 (E=0.44); 322 (E=0.44); 431 (E=0.49) nm

No change upon adding alkali.

(Concentration 50 μg/ml; layer thickness 0.2 cm).

EXAMPLE 17

(E)-2-{[[3-(Dimethylamino)propyl]amino]phenylmethylene}benzo[b]thiophen-3(2H)-one Prepared as in Example 1 from 2-benzoyl-benzo[b]-thiophen-3-ol, phosphorus(V) chloride and an aqueous solution of 3-(dimethylamino)-propylamine (prepared from 51 gm of diamine and 70 cc of water) with a yield of 26% of theory.

M.p. 90°-91° C. (ethyl acetate/petroleum ether 1:1).

$C_{20}H_{22}N_2OS$ (338.47): Calc.: C-70.97%; H-6.55%; N-8.28%; S-9.47%; Found: C-70.83%; H-6.67%; N-8.31%; S-9.29%.

EXAMPLE 18

(E)-2-{[(2-Hydroxyethyl)amino]phenylmethylene}-benzo[b]-thiophen-3(2H)-one

Prepared as in Example 1 from 2-benzoyl-benzo[b]thiophen-3-ol, phosphorus(V) chloride and an aqueous 40% ethanolamine solution with a yield of 13% of theory. M.p. 122°–123° C. (ethyl acetate/petroleum ether 1:1)

$C_{17}H_{15}NO_2S$ (297.38): Calc.: C-68.66%; H-5.08%; N-4.71%; S-10.78%; Found: C-68.65%; H-4.89%; N-4.71%; S-11.00%.

IR($CH_2Cl_2$): O—H 3620, N—H or O—H (associated), 3340 broad, C=O approx. 1600 cm$^{-1}$ UV (ethanol): λ max (neutral) 226 (E=0.58); 2.63 (E=0.68); 336 (E=0.86); 4.60 (E=0.50) nm λ max (alkaline) 257–261 (E=0.60), 336 (E=0.63); 4.59 (E=0.36) nm.

EXAMPLE 19

(E)-2-[(Amino)-(2-methylphenyl)methylene]-benzo[b]thiophen-3(2H)-one

Prepared as in Example 1 from 2-(2-methylbenzoyl)-benzo-[b]-thiophen-3-ol, phosphorus(V) chloride and concentrated aqueous ammonia with a yield of 50% of theory.

M.p. 143°–144° C. (ethyl acetate/petroleum ether 1:1)

$C_{16}H_{13}NOS$ (267.34): Calc.: C-71.88%; H-4.90%; N-5.24%; S-11.99%; Found: C-72.23%; H-5.04%; N-5.27%; S-11.70%

IR($CH_2Cl_2$): 3480 (N—H), O—H associated or NH associated; approx: 1600 cm$^{-1}$(C=O)

UV (ethanol): λ max (neutral) 260 shoulder (E=0.48); 285 (E=0.59); 311 (E=0.57); 4.22 (E=0.59) nm λ max (alkaline) 285 (E=0.64); 310 (E=0.45); 421 (E=0.42); shoulder at 404 (E=0.40) nm.

Concentration: 50 μg/ml; layer thickness 0.2 cm).

EXAMPLE 20

(E)-2-{[(Ethyl)amino]phenylmethylene}-benzo[b]thiophen-3-(2H)-one

Prepared as in Example 1 from 2-benzoyl-benzo[b]thiophen-3-ol, phosphorus(V) chloride and an aqueous 30% ethylamine solution with a yield of 56% of theory.

M.p. 115°–116° C. (ethyl acetate/petroluem ether 1:1).

$C_{17}H_{15}NOS$ (281.38): Calc.: C-72.57%; H-5.37%; N-4.98%; S-11.39%; Found: C-72.43%; H-5.53%; N-4.89%; S-11.65%.

EXAMPLE 21

(E)-2-{[(Methylethyl)amino]phenylmethylene}-benzo[b]thiophen-3-(2H)-one

Prepared as in Example 1 from 2-benzoyl-benzo[b]thiophen-3-ol, phosphorus(V) chloride and an aqueous 38.5% isopropylamine solution with a yield of 54% of theory. M.P. 112°–113° C. (ethyl acetate/petroleum ether 1:1).

$C_{18}H_{17}NOS$ (295.40): Calc.: C-73.19%; H-5.80%; N-4.74%; S-10.85%; Found: C-73.15%; H-5.99%; N-4.61%; S-10.80%.

IR($CH_2C_{12}$): C=O approx. 1590 cm$^{-1}$

UV (ethanol): λ max (neutral) 286, 321, 429 shoulder at 260 nm; no displacement upon adding alkali $^1$H-NMR (CDCl$_3$, 80 MHz): δ11.88 (1H, broad, internal H bridge); 7.95 (1H-dd, J=7 Hz and 2 Hz; ar.H); 7.7-7.15 (8H-m; ar.H); 3.9–3.4 (1H-m

1.24 (6H-d; J=6 Hz; (CH$_3$)$_2$).

EXAMPLE 22

(E)-2-[(Amino)(3-methyl-phenyl)methylene]-benzo[b]thiophen-3(2H)-one

Prepared as in Example 1 from 2-(3-methylbenzoyl)-benzo[b]-thiophen-3-ol, phosphorus(V) chloride and concentrated ammonia with a yield of 36% of theory. M.p. 114°–115° C. (ethyl acetate/petroleum ether 1:1)

$C_{16}H_{13}NOS$ (267.34): Calc.: C-71.88%; H-4.90%; N-5.24%; S-11.99%; Found: C-71.95%; H-4.91%; N-5.56%; S-12.17%.

EXAMPLE 23

(E)-2-[(Amino)-(2-ethylphenyl)methylene]-benzo[b]thiophen-3(2H)-one

Prepared as in Example 1 from 2-(ethyl-benzoyl)benzo[b]-thiophen-3-ol, phosphorus(V) chloride and concentrated ammonia with a yield of 46% of theory. M.p. 132°–133° C. (ethyl acetate/petroleum ether 1:1).

$C_{17}H_{15}NOS$ (281.38): Calc.: C-72.57%; H-5.37%; N-4.98%; S-11.39%; Found: C-72.95; H-5.58%; N-5.05%; S-11.56%.

IR(KBr): 3500–3000 N—H associated, approx. 1600 cm$^{-1}$ C=O

UV (ethanol): λ max (neutral) 260–274 (E=0.42); 284 (E=0.52); 312 (E=0.51); 422 (E=0.53); shoulder at 410 nm λ max (alkaline) 284 (E=0.56); 312 (E=0.41); 422 (E=0.41; shoulders at 260 (E=0.37) and 404 (E=0.38) nm (Concentration: 50 μg/ml; layer thickness: 0.2 cm).

EXAMPLE 24

(E)-2-{[(Methyl)amino]-2-(ethyl-phenyl)methylene}-benzo[b]thiophen-3(2H)-one

Prepared as in Example 1 from 2-(2-ethyl-benzoyl)-benzo[b]-thiophen-3-ol, phosphorus(V) chloride and an aqueous 25% methylamine solution with a yield of 42% of theory. M.p. 126°–127° C. (ethyl acetate/petroleum ether 1:1)

$C_{18}H_{17}NOS$ (295.40): Calc.: C-73.19%; H-5.80%; N-4.74%; S-10.85%; Found: C-73.30%; H-5.67%; N-4.85%; S-10.89%.

IR($CH_2Cl_2$): C=O approx. 1600 cm$^{-1}$

UV (ethanol): λmax (neutral) 266–274, 289, 318, 429, a shoulder at 412 nm; no change upon adding alkali.

$^1$H-NMR (CDCl$_3$; 80 MHz): δ 11.73 (1H, broad, internal H bridge); 7.97 (1H-d, broadened, J=6.5 Hz, ar. H; 7.7–7.0 (7H-m; ar. H); 2.83 (3H-d. J=2.5 Hz; N—CH$_3$); 2.64 (2H-q, J=7.2 Hz; —CH$_2$—); 1.19 (3H-t; J=7.2 Hz; C—CH$_3$).

EXAMPLE 25

(E)-2-{[(Ethyl)amino]-(2-ethyl-phenyl)methylene}-benzo[b]-thiophen-3(2H)-one

Prepared as in Example 1 from 2-(2-ethyl-benzoyl)-benzo-[b]thiophen-3-ol, phosphorus(V) chloride and an aqueous 25% ethylamine solution with a yield of 2% of theory. M.p. 76°–77° C. (diisopropyl ether/petroleum ether 1:2).

$C_{19}H_{19}NOS$ (309.43): Calc.: C-73.75%; H-6.19%; N-4.53%; S-10.36%; Found: C-74.05%; H-6.16%; N-4.58%; S-10.35%.

EXAMPLE 26

(E)-2-[(Amino)-(2-nitrophenyl)methylene]-benzo[b]thiophen-3(2H)-one

Prepared as in Example 1 from 2-(2-nitrobenzoyl)-benzo[b]-thiophen-3-ol, phosphorus(V) chloride and concentrated aqueous ammonia with a yield of 21% of theory. M.p. 185°–186° C. (ethyl acetate).

$C_{15}H_{10}N_2O_3S$ (298.32): Calc.: C-60.39%; H-3.38%; N-9.39%; S-10.75%; Found: C-60.23%; H-3.42%; N-9.34%; S-10.79%

IR($CH_2Cl_2$): N—H 3480 (also N-H associated), C=O approx. 1600, $NO_2$ 1350 and 1515–1535 $cm^{-1}$ UV (ethanol): λ max (neutral) 261 (E=0.52); 287 (E=0.51); 313 (E=0.47); 423 (E=0.40) nm; λ max (alkaline) 246 (E=0.35); 286 (E=0.64); 312 (E=0.20); 383 (E=0.33) nm;

(Concentration: 50 μg/ml; layer thickness: 0.2 cm).

EXAMPLE 27

(E)-2-{[(1,1-Dimethylethyl)amino]phenylmethylene}-benzo[b]-thiophen-3(2H)-one

Prepared as in Example 1 from 2-benzoyl-benzo[b]thiophen-3-ol, phosphorus(V) chloride and an aqueous 40% solution of 1,1-dimethylamine with a yield of 57% of theory.

M.p. 131°–132° C. (ethyl acetate/petroleum ether 1:1)

$C_{19}H_{19}NOS$ (309.43): Calc.: C-73.75%; H-6.19%; N-4.53%; S-10.36%; Found: C-73.40%; H-6.25%; N-4.48%; S-10.34%

IR($CH_2Cl_2$): N—H associated, C=O approx. 1600, C=C 1610 $cm^{-1}$

UV (ethanol): λ max (neutral) 264, 288, 324, 416 (shoulder), 432 nm; no change upon adding alkali;

$^1$H-NMR(CDCl$_3$, 80 MHz): δ 12.35 (1H-s, broad, internal H bridge) 7.96 (1H-dd, J=7 Hz and 2 Hz; ar.H); 7.65–7.1 (8H-m; ar. H); 1.28 (9H-s; —C(CH$_3$)$_3$).

EXAMPLE 28

(E)-2-[(Amino)-(2-bromo-phenyl)methylene]-benzo[b]thiophen-3(2H)-one

Prepared as in Example 1 from 2-(2-bromobenzoyl)-benzo[b]-thiophen-3-ol, phosphorus(V) chloride and concentrated aqueous ammonia with a yield of 42% of theory. M.p. 143°–144° C. (petroleum ether/ethyl acetate 1:1).

$C_{15}H_{10}BrNOS$ (332.22): Calc.: C-54.23%; H-3.03%; Br-24.05%; N-4.22%; S-9.65%; Found: C-54.10%; H-3.04%; Br-24.25%; N-4.13%; S-9.56%.

EXAMPLE 29

(E)-2-{[(2-propynyl)amino]phenylmethylene}-benzo[b]thiophen-3-(2H)-one

Prepared as in Example 1 from 2-benzoyl-benzo[b]thiophen-3-ol, phosphorus(V) chloride and an aqueous propargylamine solution obtained by reacting a solution of 10 gm of propargylamine hydrochloride in 10 cc of water with a solution of 10.6 gm of anhydrous sodium carbonate in 20 cc of water, with a yield of 46% of theory.

M.p. 126°–128° C. (ethyl acetate/petroleum ether 1:1).

$C_{18}H_{13}NOS$ (291.37): Calc.: C-74.20%; H-4.50%; N-4.81%; S-11.00%; Found: C-74.04%; H-4.47%; N-4.70%; S-11.05%. p IR($CH_2Cl_2$): —C≡C—H 3300, C=O approx. 1600 $cm^{-1}$; also associated H;

UV (ethanol): λ max (neutral) 266–276 (E=0.45); 286 (E=0.48); 319 (E=0.56); 434 (E=0.54); λ max (alkaline) 255 (E=0.70); 313 (E=0.34); 434 (E=0.22).

(Concentration: 50 μg/ml: layer thickness 0.2 cm).

$^1$H-NMR(CDCl$_3$, 80 MHz): δ 11.75 (1H, broad, internal H bridge); 7.95 (1H-dd, J=7 Hz and 2 Hz; ar. H); 7.7–7.1 (8H-m; ar. H); 3.94 (2H-dd, J=6 Hz and 2.5 Hz; —CH$_2$—); 2.32 (1H-t; J=2.5 Hz).

EXAMPLE 30

(E)-2-[(Amino)phenylmethylene]-benzo[b]thiophen-3(2H)-one

A mixture of 10.0 gm (0.0393 mol) of 2-benzoylbenzo[b]-thiophen-3-ol, 60 cc of concentrated aqueous ammonia and 250 cc of ethanol was heated for 20 hours at a temperature of 120° C. after introducing 5 bar of ammonia gas into the vessel. After cooling, the mixture was stirred into 1.5 liters of water, the precipitated pale yellow reaction product was filtered off with suction, washed thoroughly several times with 50 cc each of water and dried in the air. 4.23 gm (42% of theory) of yellow crystals, m.p. 121°–122° C., were obtained (after twice recrystallizing from petroleum ether/ethyl acetate 1:1 using activated carbon) and were found to be completely identical with the product obtained in Example 1 based on elemental analysis, IR and UV spectra.

After keeping the above reaction mixture for 15 hours at 150° C., the yield was 5% of theory; after keeping it for 15 hours at 80° C., the yield drops to 22% of theory; and after heating it for 15 hours at 40° C. and then heating for 10 hours at 60° C., the yield was 31% of theory.

EXAMPLE 31

(E(-2-[(Amino)phenylmethylene]-benzo[b]-thiophen-3(2H)-one 35.1 gm (0.138 mol) of 2-benzoyl-benzo[b]thiophen-3-ol were dissolved in 35 cc of glacial acetic acid, followed by the addition of 39.0 gm (0.506 mol) of ammonium acetate and refluxing for two and a half hours. The still warm mixture was stirred into 300 cc of ice water, whereby a reddish product was precipitated. The solid was filtered off, dried in the air and recrystallized once from 60 cc of toluene. For further purification, it was dissolved in 30 cc of ethyl acetate, and just enough petroleum ether was added to ensure that no further precipitate forms (about 20 cc), after which 20 gm of activated carbon was added, followed by boiling and hot filtering. The pure end product was obtained from the cool filtrate by cooling to +10° C., adding 60 cc of petroleum ether, allowing the mixture to stand for two hours, and then suction-filtering. By concentrating the mother liquors to a volume of 30 cc and prolonged cooling to +10° C., 2.0 gm more of the desired product of the same quality were obtained. The combined crystalline product was thoroughly washed with a total of 20 cc of petroleum ether and freed from solvents in a circulating air drier at +70° C. 23.0 gm (66% of theory) of egg yellow crystals were obtained, m.p. 121.6°–122.5° C., and were found to be identical with the product of Example 1 based on elemental analysis, IR and UV spectra.

EXAMPLE 32

(E)-2-{[(Cyclohexyl)amino]phenylmethylene}-benzo[b]thiophen-3(2H)-one

Prepared as in Example 31 with a yield of 56% of theory from 2-benzoyl-benzo[b]thiophen-3-ol and cyclohexylamine. Lemon-yellow crystals were obtained, m.p. 122°–123° C. (petroleum ether/ethyl acetate 85:15).

$C_{21}H_{21}NOS$ (335.46): Calc.: C-75.19%; H-6.31%; N-4.18%; S-9.56%; Found: C-74.93%; H-6.27%; N-4.17%; S-9.54%

IR($CH_2Cl_2$): C=O about 1600 $cm^{-1}$, C=C 1610 $cm^{-1}$

UV (ethanol): λ max (neutral) 288 (E=0.47), 323 (E=0.46); 432 (E=0.50); no displacement after adding alkali;

$^1$H-NMR ($CDCl_3$; 80 MHz): δ 12.3–11.8 (1H-m, broad, internal H bridge); 7.98 (1H-dd, J=7 Hz and 2 Hz; ar.H); 7.7–7.1 (8H-m. ar. H); 3.6–3.1 (1H-m;

2.1–1.0 (10H-m; cyclohexyl).

EXAMPLE 33

(E)-2-[(Amino)phenylmethylene]-benzo[b]thiophen-3(2H)-one

Prepared as in Example 31, but using (E)-2-[(methoxy)phenylmethylene]-benzo[b]thiophen-3(2H)-one instead of 2-benzoyl-benzo[b]thiophen-3-ol, and reduction of the reaction time to 10 minutes, with a yield of 72% of theory.

Egg-yellow crystals, m.p. 121°–122° C., completely identical with the product of Example 1 based on TLC, mixed melting point, elemental analysis and IR spectrum.

EXAMPLE 34

(E)-2-[(Amino)phenylmethylene]-benzo[b]thiophen-3(2H)-one

A mixture of 10.0 gm (0.0373 mol) of (E)-2-[(methoxy)phenylmethylene]-benzo[b]thiophen-3(2H)-one, 75 cc of concentrated ammonia and 250 cc of methanol was refluxed for 10 minutes. After cooling, the mixture was stirred into 1.5 liters of ice water, the precipitated reaction product was filtered off with suction, washed thoroughly with water and dried in the air. For purification, the crude product was dissolved in 100 cc of ethyl acetate, followed by the addition of ethereal hydrochloric acid until no further precipitate formed, followed by filtering and washing of the filter residue with ethyl acetate. The solid was suspended in 100 cc of water, and the suspension was made alkaline with ammonia, and again filtered with suction. After drying and recrystallizing from petroleum ether/ethyl acetate, 4.7 gm (50% of theory) of the title compound, m.p. 121°–122° C., were obtained and found to be identical with the product obtained in Example 1 based on TLC, mixed melting point and elemental analysis.

EXAMPLE 35

(E)-2-[(Amino)phenylmethylene]-benzo[b]thiophen-3(2H)-one

A mixture of 35.0 gm (0.138 mol) of 2-benzoylbenzo[b]-thiophen-3-ol, 24.0 gm (0.311 mol) of ammonium acetate and 25 cc of dimethylsulfoxide was stirrd for one hour at a reaction temperature of 125° C. The cooled reaction mixture was stirred into a mixture of 150 cc of petroleum ether and 300 cc of ice water. The resulting suspension was filtered with suction, and the filter residue was thoroughly washed with water. For purification purposes, the dried crude product was taken up in 40 cc of ethyl acetate, and just enough petroleum ether was added to ensure that no further precipitate formed (about 20 cc). 5 gm of activated carbon were added, followed by boiling and filtering while hot. The pure product was obtained from the crude filtrate by adding 60 cc of petroleum ether and cooling to +10° C. Further product of the same quality was obtained by concentrating the mother liquor to approximately 30 cc total volume. The combined crystalline product was washed with petroleum ether and dried in vacuo, yielding 25.2 gm (72% of theory) of the desired product, m.p. 121.6°–122.5° C., which was found to be identical with that of Example 1 based on its thin-layer chromatogram, mixed melting point and IR spectrum.

EXAMPLE 36

(E)-2-{[[2-(4-Morpholinyl)ethyl]amino]phenylmethylene}benzo-[b]thiophen-3(2H)-one Prepared as in Example 35 from 2-benzoyl-benzo[b]thiophen-3-ol and 2-(4-morpholinyl)-ethylamine instead of ammonium acetate with a yield of 62% of theory.

$C_{21}H_{22}N_2O_2S$ (366.48): Calc.: C-68.83%; H-6.05%; N-7.64%; S-8.75%; Found: C-68.60%; H-6.20%; N: 7.70%; S-8.80%

IR($CH_2Cl_2$): N—H associated 3200–3600, C=O approx. 1600 $cm^{-1}$

UV (ethanol): λ max (neutral) 275 (shoulder), 288, 322, 433 nm; no displacement upon adding alkali.

$^1$H-NMR($CDCl_3$; 80 MHz): 11.84 (1H, broad, internal H-bridge); 7.97 (1H-dd, J=6.5 and 2 Hz; ar. H); 7.7–7.1 (8H-m; ar. H); 3.9–3.6 (4H-m; —$CH_2O$—$CH_2$—); 3.5–3.2 (2H-m; —N—$CH_2$—); 2.7–2.3 (6H-m;

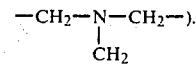

EXAMPLE 37

(E)-2-{[(Propyl)amino]phenylmethylene}-benzo[b]thiophen-3-(2H)-one

Prepared as in Example 35 from 2-benzoyl-benzo[b]thiophen-3-ol and n-propylammonium acetate with a yield of 68% of theory; m.p. 124°–125° C. (petroleum ether/ethyl acetate 1:1).

$C_{18}H_{17}NOS$ (295.40): Calc.: C-73.19%; H-5.80%; N-4.74%; S-10.85%; Found: C-72.80%; H-5.88%; N-4.89%; S-10.95%.

EXAMPLE 38

(E)-2-{[(Butyl)amino]phenylmethylene}-benzo[b]thiophen-3(2H)-one

Prepared as in Example 35 from 2-benzoyl-benzo[b]thiophen-3-ol and n-butylammonium acetate with a yield of 64% of theory; m.p. 106°-107° C. (petroleum ether/ethyl acetate 1:1).

$C_{19}H_{19}NOS$ (309.43): Calc.: C-73.75%; H-6.19%; N-4.53%; S-10.36%; Found: C-73.40%; H-6.13%; N-4.64%; S-10.44%.

EXAMPLE 39

(E)-2-{[(2-Methylpropyl)amino]phenylmethylene}-benzo[b]thiophen-3(2H)-one

Prepared as in Example 35 from 2-benzoyl-benzo[b]thiophen-3-ol and (2-methylpropyl)ammonium acetate with a yield of 69% of theory; m.p. 125°-126° C. (ethyl acetate/petroleum ether 1:2).

$C_{19}H_{19}NOS$ (309.43): Calc.: C-73.75%; H-6.19%; N-4.53%; S-10.36%; Found: C-76.60%; H-6.21%; N-4.68%; S-10.30%.

IR(CH$_2$Cl$_2$): N—H associated 3200-3600; C=O approx. 1600 cm$^{-1}$

UV (ethanol): λ max (neutral) 270 (shoulder), 288, 323, 432 nm; no displacement upon adding alkali.

$^1$H-NMR (CDCl$_3$/D$_2$O; 80 MHz); 7.94 (1H-dd, J=6.5 and 2 Hz; ar. H); 7.7-7.1 (8H-m; ar. H); 3.05 (2H-d; J=6.5 Hz; N—CH$_2$—C; 2.1-1.5 (1H-m;

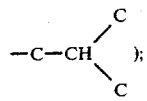

0.95 (6H-d; J=6.5 Hz; —C(CH$_3$)$_2$).

EXAMPLE 40

(E)-2-[(Dimethylamino)phenylmethylene]-benzo[b]thiophen-3(2H)-one

Prepared as in Example 31 from 2-benzoyl-benzo[b]thiophen-3-ol and dimethylammonium acetate with a yield of 18% of theory; m.p. 179°-180° C. (ethyl acetate/petroleum ether 1:2). The product was identical to that prepared according to Example 4, based on its thin-layer chromatogram, elemental analysis and IR-spectrum.

EXAMPLE 41

(E)-2-[(Amino)phenylmethylene]-benzo[b]thiophen-3(2H)-one

A mixture of 5.0 gm (0.0197 mol) 2-benzoylbenzo[b]thiophen-3-ol, 12.0 gm (0.156 mol) of ammonium acetate and 5 cc of 1,2-ethanediol was heated for two hours at 130° C., accompanied by stirring. The cooled mixture was stirred into 50 cc of ice water, followed by filtering with suction and column-chromatographic purification of the filter residue on silica gel, using 1,2-dichloroethane as the eluant. Recrystallization from petroleum ether/ethylene acetate (2:1) yielded 2.5 gm (50% of theory) of egg-yellow crystals, m.p. 121°-122° C., which based on TLC, mixed melting point and elemental analysis were identical to the product of Example 1.

EXAMPLE 42

(E)-2-[(Amino)phenylmethylene]-benzo[b]thiophen-3(2H)-one

Prepared as in Example 41 from 2-benzoyl-benzo[b]thiophen-3-ol, but using urea instead of ammonium acetate, with a yield of 55% of theory; m.p. 121°-122° C. (petroleum ether/ethyl acetate 2:1). The product was identical to that of Example 1, based on its TLC, mixed melting point and IR-spectrum.

EXAMPLE 43

(E)-2-[(Amino)phenylmethylene]-benzo[b]thiophen-3(2H)-one 5.0 gm (0.0186 mol) of (E)-2-[(methoxy)phenylmethylene]-benzo[b]thiophen-3(2H)-one and 10.0 gm (0.167 mol) of urea are thoroughly admixed and heated for 10 minutes at a temperature between 125° and 130° C. The cold product was column-chromatographically purified as described in Example 41, yielding 3.84 gm (81% of theory) of egg-yellow crystals, m.p. 121°-122° C. (petroleum ether/ethyl acetate 2:1), which were identical to the product of Example 1, based on its TLC, mixed melting point, elemental analysis and IR spectrum.

EXAMPLE 44

(E)-2-[(Amino)phenylmethylene]-benzo[b]thiophen-3(2H)-one

When 2-benzoyl-benzo[b]thiophen-3-ol was reacted with the following reagents in place of ammonium acetate under the conditions of Example 35, the title compound was obtained, characterized in each case by its thin-layer chromatogram, mixed melting point, elemental analysis and IR spectrum, with the yields shown to the right below:

Ammonium oxalate: 42% of theory
Ammonium carbonate: 64% of theory
Ammonium formate: 74% of theory
Ammonium propionate: 66% of theory
Ammonium carbamate: 59% of theory
Diammonium hydrogen citrate: 61% of theory.

EXAMPLE 45

(E)-2-[(Amino)phenylmethylene]-benzo[b]thiophen-3(2H)-one

When 2-benzoyl-benzo[b]thiophen-3-ol was reacted with the following reagents instead of with ammonium acetate under the conditions of Example 31, the title compound, m.p. 121°-122° C. (petroleum ether/ethyl acetate 2:1), was obtained with the yields given to the right below:

Ammonium formate: 78% of theory
Formamide: 70% of theory
Ammonium thiocyanate: 33% of theory
Triammonium phosphate: 27% of theory.

EXAMPLE 46

(E)-2-[(Methylamino)phenylmethylene]-benzo[b]thiophen-3(2H)-one

Prepared as in Example 31 from 2-benzoyl-benzo[b]thiophen-3-ol, but using N,N'-dimethylurea in place of ammonium acetate, with a yield of 66% of theory, m.p. 156°-157° C. (ethyl acetate). On the basis of its thin-layer chromatogram, mixed melting point, elemental analysis and IR spectrum, the product was identical to that of Example 2.

EXAMPLE 47

(E)-2-[(Amino)-(2-bromophenyl)methylene]-benzo[b]thiophen-3(2H)-one

Prepared as in Example 31 from 2-(2-bromobenzoyl)-benzo[b]thiophen-3-ol and formamide in place of ammonium acetate with a yield of 10% of theory, m.p. 143°–144° C. (petroleum ether/ethyl acetate 1:1). The thin-layer chromatogram, mixed melting point, elemental analysis and IR spectrum showed it to be identical to the product of Example 28.

EXAMPLE 48

(E)-2-[(Amino)phenylmethylene]-benzo[b]thiophen-3(2H)-one

Prepared as in Example 35, but using 2-benzoyl-3-chloro-benzo[b]thiophene in place of 2-benzoyl-benzo[b]thiophen-3-ol, with a yield of 9% of theory; m.p. 120°–121° C. (ethyl acetate/petroleum ether 1:2). The TLC, IR and UV spectra showed it to be identical to the product of Example 1.

EXAMPLE 49

(E)-2-[(Amino)phenylmethylene]-benzo[b]thiophen-3(2H)-one 0.5 gm (0.00186 mol) of (E)-2-[(hydroxyamino) phenylmethylene]-benzo[b]thiophen-3(2H)-one, dissolved in 10 cc of glacial acetic acid, was catalytically hydrogenated for 2½ hours at a hydrogen pressure of 5 bar in the presence of 0.2 gm of platinum(IV) oxide. At the end of the hydrogen uptake, the catalyst-free solution was stirred into 100 cc of water, exhaustively extracted with ether, the combined ether extracts are successively washed with water, saturated aqueous sodium bicarbonate solution and then again with water, followed by drying over sodium sulfate. The crystalline residue left behind after expelling the solvent was recrystallized twice in the presence of activated carbon from a mixture of petroleum ether and ethyl acetate (2:1). 0.37 gm (79% of theory) of egg-yellow crystals, m.p. 121°–122° C., were obtained which, on the basis of the thin-layer chromatogram, mixed melting point and IR spectrum, were found to be identical to the product obtained according to Example 1.

EXAMPLE 50

(E)-2-[(Amino)phenylmethylene]-benzo[b]thiophen-3(2H)-one

Prepared as in Example 49 from (E)-2-[(2-phenylhydrazino)phenylmethylene]-benzo[b]thiophen-3(2H)-one with a yield of 48% of theory; m.p. 121°–122° C. (ethyl acetate/petroleum ether 1:2). The thin-layer chromatogram, mixed melting point and IR spectrum showed the product to be identical to that of Example 1.

EXAMPLE 51

(E)-2-[(Amino)phenylmethylene]-benzo[b]thiophen-3(2H)-one 0.5 gm (0.00145 mol) of (E)-2-[(phenyl-hydrazino)-phenylmethylene]-benzo[b]thiophen-3(2H)-one (m.p. 168° C. after recrystallization from methanol/acetone 1:1) was suspended in 5 cc of an aqueous 2% sodium hydroxide solution, 1.0 gm (0.00476 mol) of sodium dithionite dihydrate was added, and the mixture was refluxed for two hours. After cooling, the mixture was extracted with 1,2-dichloroethane, the organic solvent was evaporated, and the residue was purified by column chromatography on silica gel using 1,2-dichloroethane as the eluant. After recrystallization from petroleum ether/ethyl acetate (2:1), yielding 0.22 gm (54% of theory) of bright yellow crystals, m.p. 121°–122° C., which, on the basis of the TLC, mixed melting point and IR spectrum were identical to the product of Example 1.

EXAMPLE 52

(E)-2-[(Amino)phenylmethylene]-benzo[b]thiophen-3(2H)-one

Prepared as in Example 51, but using (E)-2-[(hydroxyamino)-phenylmethylene]-benzo[b]thiophen-3(2H)-one as the starting substance, with a yield of 47%, m.p. 121°–122° C. (petroleum ether/ethyl acetate 2:1). According to the thin-layer chromatogram, melting point and IR spectrum, the product was identical to that of Example 1.

EXAMPLE 53

(E)-2-[(Amino(phenylmethylene)-benzo[b]thiophen-3(2H)-one 0.5 gm (0.00145 mol) of (E)-2-[(2-phenyl-hydrazino)-phenylmethylene]-benzo[b]thiophen-3(2H)-one was dissolved in 10 cc of glacial acetic acid and 5 cc of 20% hydrochloric acid, and 1.0 gm of iron powder was added. The maintenance of a reaction temperature of 15° to 23° C. was ensured by external cooling with water. After one hour the mixture was worked up as in Example 49. 0.33 gm (90% of theory) of the title compound, m.p. 121°–122° C. (petroleum ether/ethyl acetate 2:1), was obtained which, according to the TLC, mixed melting point and elemental analysis, was identical to the product of Example 1.

EXAMPLE 54

(E)-2-[(1-Pyrrolidinyl)phenylmethylene]-benzo[b]thiophen-3(2H)-one

Prepared as in Example 31 from 2-benzoyl-benzo[b]thiophen-3-ol and pyrrolidine in glacial acetic acid with a yield of 5% of theory. Egg-yellow crystals, m.p. 157° C. (ethyl acetate/petroleum ether 1:3).

$C_{19}H_{17}NOS$ (307.41): Calc.: C-74.24%; H-5.57%; N-4.56%; S-10.43%; Found: C-74.69%; H-5.66%; N-4.60%; S-10.67%

IR(CH$_2$Cl$_2$): C=O 1600 cm$^{-1}$

UV (ethanol): λ max 266–290 (E=0.38), 325 (E=0.45), 440 (E=0.49) nm $^1$H-NMR(CDCl$_3$, 80 MHz): δ7.93 (1H)-dd, J=7 and 2 Hz; ar. H); 7.7–7.2 (8 H-m; ar. H); 4.1–3.3 (4 H-m, broad, —CH$_2$—N—CH$_2$—); 1.8–2.2 (4 H-m, —C—CH$_2$CH$_2$—C).

EXAMPLE 55

(E)-2-[(Amino)-(2-trifluoromethyl-phenyl)methylene]-benzo[b]thiophen-3(2H)-one

Prepared as in Example 1 from 2-(2-trifluoromethyl-benzoyl)-benzo[—]thiophen-3-ol, phosphorus(V) chloride and concentrated ammonia with a yield of 6% of theory; m.p. 148°–149° C. (petroleum ether/ethyl acetate 2:1).

$C_{16}H_{10}F_3NOS$ (321.31): Calc.: C-59.81%; H-3.14%; N-4.36%; Found: C-59.99%; H-3.49%; N-4.27%.

EXAMPLE 56

(E)-2-[(Amino)-(2-Amino-phenyl)methylene]-benzo[b]-thiophen-3(2H)-one 0.5 gm (0.00168 mol) of (E)-2-[(amino)-(2-nitrophenyl)methylene]-benzo[b]thiophen-3(2H)-one was dissolved in a mixture of 10 cc of methyl acetate and 10 cc of tetrahydrofuran, and after adding 0.5 gm of Raney nickel the mixture was hydrogenated at room temperature and a hydrogen pressure of 5 bar until hydrogen uptake was at an end. The catalyst was then filtered off, the solvent was evaporated at reduced pressure, and the residue was recrystallized twice in the presence of activated charcoal from tetrahydrofuran/petroleum ether (1:1). 330 mgm (73% of theory) of yellow crystals were obtained, m.p. 186°–187° C. (petroleum ether/tetrahydrofuran 1:1).

$C_{15}H_{12}N_2OS$ (268.34): Calc.: C-67.14%, H-4.51%; N-10.44%, S-11.95%; Found: C-66.73%; H-4.84%; N-9.82%; S-11.75%.

EXAMPLE 57

(E)-2-{[(Cyclopropyl)amino]phenylmethylene}-benzo[b]thiophen-3(2H)-one

Prepared as in Example 31 with a yield of 25% of theory from 2-benzoyl-benzo[b]thiophen-3-ol and cyclopropylamine. Egg-yellow crystals, m.p. 131°–132° C. (petroleum ether/ethyl acetate 1:1).

$C_{18}H_{15}NOS$ (293.39): Calc.: C-73.69%; H-5.15%; N-4.77%; S-10.93%; Found: C-73.28%; H-5.38%; N-4.75%; S-11.10%

IR(CH$_2$Cl$_2$): internal H-bridge, C=0 1595 cm$^{-1}$

UV (ethanol); λ max 266–276 (E=0.44); 286 (E=0.46); 321 (E=0.49); 435 (E=0.54) nm (Concentration: 50 μg/ml; layer thickness 0.2 cm)

$^1$H-NMR (CDCl$_3$/CD$_3$OD; 80 MHz); δ7.96 (1$^1$H-dd, J=7 Hz and 2 Hz; ar. H); 7.6–7.1 (8 H-m; ar.H);

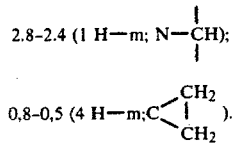

EXAMPLE 58

(E)-2-[(Amino)phenylmethylene]-benzo[b]thiophen-3(2H)-one 0.5 gm (0.00186 mol) of (E)-2-[(hydroxyamino)-phenylmethylene]-benzo[b]thiophen-3(2H)-one were dissolved in 20 cc of tetrahydrofuran, the solution was successively admixed with a solution of 1.05 gm (0.038 mol) of iron(II) sulfate heptahydrate in 2 cc of water and 1 drop of concentrated hydrochloric acid and with 3 cc of concentrated ammonia, and the mixture was stirred for 3 hours at room temperature, followed by heating at 90° C. for 5 minutes. The cooled mixture was stirred into 100 cc of water and exhaustively extracted with ether. The ether extracts were washed with water, dried over sodium sulfate, and the crystalline residue which remained after expelling the solvent was recrystallized twice from a mixture of petroleum ether and ethyl acetate (2:1) in the presence of activated charcoal. 0.24 gm (51% of theory) of egg-yellow crystals, m.p. 121°–122° C., was obtained which, according to the thin-layer chromatogram, mixed melting point, elemental analysis and IR spectrum, were identical to the product of Example 1.

EXAMPLE 59

(E)-2-[(Ammonia)phenylmethylene]-benzo[b]thiophen-3(2H)-one

A mixture of 0.5 gm (0.00145 mol) of (E)-2-[(2-phenyl-hydrazino)-phenylmethylene]-benzo[b]thiophen-3(2H)-one, 1.0 gm (0.00443 mol) of tin(II) chloride dihydrate and 5 cc of concentrated hydrochloric acid was magnetically stirred for 24 hours at room temperature. The resulting clear solution was evaporated in vacuo to a viscous paste, then admixed with 10 cc of water and adjusted to pH 7 by the dropwise addition of 10% ammonia solution. The resulting suspension was exhaustively extracted with ethyl acetate, the combined organic extracts were dried over sodium sulfate and concentrated under reduced pressure, and the residue was purified column-chromatographically on silica gel, using 1,2-dichloroethane as the eluant. After recrystallization from petroleum ether/ethyl acetate (2:1), 0.21 gm (57% of theory) of egg-yellow crystals, m.p. 121°–122° C., were obtained which, on the basis of the TLC, mixed melting point and elemental analysis were identical with the product of Example 1.

EXAMPLE 60

(E)-2-[(Amino)phenylmethylene]-benzo[b]thiophen-3(2H)-one 0.5 gm (0.00145 mol) of (E)-2-[(2-phenylhydrazino)-phenylmethylene]-benzo[b]thiophen-3(2H)-one was dissolved in 10 cc of anhydrous tetrahydrofuran, and the solution was stirred for 30 minutes at room temperature after adding 0.1 gm (0.00264 mol) of lithium tetrahydroaluminate. In order to decompose the excess lithium tetrahydroaluminate, 10 drops of water, 10 drops of an aqueous 15% sodium hydroxide solution and then another 50 drops of water were successively added, followed by boiling, filtering, removing the solvent from the filtrate and purification of the residue as described in Example 59. 0.085 gm (23% of theory) of egg-yellow crystals, m.p. 120°–121° C., was obtained, and the thin-layer chromatogram and mixed melting point revealed them to be identical to the product of Example 1.

EXAMPLE 61

(E)-2-[(Amino)phenylmethylene]-5-methyl-benzo[b]thiophen-3-(2H)-one

Prepared as in Example 35 from 2-benzoyl-5-methyl-benzo[b]thiophen-3-ol and ammonium acetate with a yield of 51% of theory.

M.p. 153°–154° C. (toluene).

$C_{16}H_{13}NOS$ (267.34): Calc.: C-71.88%; H-4.90%; N-5.24%; S-11.99%; Found: C-72.10%; H-5.08%; N-5.22%; S-12.15%

IR(CH$_2$Cl$_2$): NH 3470 C=0 1600 cm$^{-1}$

UV (ethanol): λ max (neutral) 266–271 (E=0.53), 325 (E=0.58), 435 (E=0.51) nm; λ max (alkaline) 279 (E=0.52), 325 (E=0.47), 433 (E=0.38) nm.

(Concentration: 50 μg/ml, layer thickness: 0.2 cm).

1H-NMR(CDCl$_3$, 80 MHz): δ10.94 (1H, broad, internal H-bridge); 7.9–7.15 (8 H-m, ar.H), 5.88 (1 H, wide, exchangeable H), 2.46 (3 H-s).

EXAMPLE 62

(E)-2-[(Amino)phenylmethylene]-6-methylbenzo[b]thiophen-3(2H)-one

Prepared as in Example 31 from 2-benzoyl-6-methyl-benzo[b]thiophen-3-ol and ammonium acetate with a yield of 57% of theory. M.p. 166°–167° C. (ethyl acetate/petroleum ether 1:1).

$C_{16}H_{13}NOS$ (267.34); Calc.: C-71.88%; H-4.90%; N-5.24%; S-11.99%; Found: C-71.70%; H-4.94%; N-5.05%; S-11.95%.

IR($CH_2Cl_2$): NH 3470, C=0 1600 cm$^{-1}$

UV (ethanol): λ max (neutral) 283 (E=0.57); 321 (E=0.55); 427 (E=0.51) nm.

(Concentration: 50 μg/ml; layer thickness: 0.2 cm).

EXAMPLE 63

(E)-2-[(Amino)phenylmethylene]-6-methoxy-benzo[b]thiophen-3(2H)-one

Prepared as in Example 31 from 2-benzoyl-6-methoxy-benzo[b]thiophen-3-ol and ammonium acetate with a yield of 64% of theory.

M.p. 147°–149° C. (toluene/petroleum ether 1:1).

$C_{16}H_{13}NO_2S$ (283.34): Calc.: C-67.82%, H-4.62%; N-4.94%; S-11.32%; Found: C-67.77%; H-4.69%; N-5.26%; S-11.85%.

EXAMPLE 64

(E)-2-[(Amino)phenylmethylene]-4-methyl-benzo[b]thiophen-3(2H)-one

Prepared as in Example 31 from 2-benzoyl-4-methyl-benzo[b]thiophen-3-ol and ammonium acetate with a yield of 50% of theory. M.p. 198°–200° C. (diisopropyl ether/ethyl acetate 2:1).

$C_{16}H_{13}NOS$ (267.34): Calc.: C-71.88%; H-4.90%; N-5.24%; Found: C-71.75%; H-5.01%; N-5.23%

IR($CH_2Cl_2$): NH 3460, C=0 1600 cm$^{-1}$

UV (ethanol): λ max (neutral) 272–275 (E=0.60); 315 (E=0.46); 433 (E=0.59) nm; λ max (alkaline) 272–275 (E=0.60); 315 (E=0.44); 433 (E=0.55) nm.

Concentration: 50 μg/ml; layer thickness: 0.2 cm).

EXAMPLE 65

(E)-2-[(Methylamino)phenylmethylene]-benzo[b]thiophen-3(2H)-one 2.53 gm (0.01 mol) of (E)-2-[(amino)phenylmethylene]-benzo[b]thiophen-3(2H)-one were dissolved in 10 ml of glacial acetic acid, followed by the addition of 20.0 (0.22 mol) of methylammonium acetate and refluxing for 5 hours. The still warm mixture was stirred into 100 ml of ice water, whereupon a reddish product precipitated. The solid was filtered off, dried in the air and, to separate small quantities of starting substance, column-chromatographically purified on silica gel using first 1,2-dichloroethane and then 1,2-dichloroethane/acetone (volume ratio 95:5) as the eluants. The egg-yellow residue left behind after evaporating the eluates was recrystallized twice from methanol. 2.05 gm (77% of theory) of yellow crystals, m.p. 155°–156° C., were obtained which were identical to the product of Example 2 according to elemental analysis, IR and UV spectra and mixed melting point.

EXAMPLE 66

(E)-2-[(Methylamino)phenylmethylene]-benzo[b]thiophen-3(2H)-one

A mixture of 2.53 gm (0.01 mol) of (E)-2-[(amino)-phenylmethylene]-benzo[b]thiophen-3(2H)-one, 40.0 gm (0.44 mol) of methylammonium acetate and 10 ml of dimethylsulfoxide was heated for 5 hours to a reaction temperature of 130° to 140° C. Working up was in accordance with Example 65, and the desired compound, m.p. 154°–155° C. (methanol), was obtained with a yield of 58% of theory. The product was identical to that of Example 2 according to elemental analysis and thin-layer chromatogram.

EXAMPLE 67

(E)-2-[(Amino)phenylmethylene]-benzo[b]thiophen-3(2H)-one 2.67 gm (0.01 mol) of (E)-2-[(methylamino)phenylmethylene]-benzo[b]thiophen-3(2H)-one were dissolved in 10 ml of glacial acetic acid, followed by the addition of 25.0 gm (0.32 mol) of ammonium acetate and refluxing for 15 minutes. After working up as in Example 65, 1.85 gm (73% of theory) of yellow crystals, m.p. 121°–122° C. (petroleum ether/ethyl acetate 2:1), were obtained which, according to the mixed melting point and IR and UV spectra, were identical to the product of Example 1.

EXAMPLE 68

(E)-2-[(Amino)phenylmethylene]-benzo[b]thiophen-3(2H)-one

The procedure was as in Example 67, but 0.32 mol of urea was used instead of ammonium acetate. After corresponding working up, 1.92 gm (76% of theory) of yellow crystals, m.p. 121°–122° C. (petroleum ether/ethyl acetate 2:1), were obtained which, on the basis of elemental analysis, mixed melting point and thin-layer chromatogram were identical to the product of Example 1.

The compounds of the present invention, that is, those embraced by formula I above, have useful pharmacodynamic properties. More particularly, they exhibit anticonvulsant activity in warm-blooded animals, such as mice.

The anticonvulsant property and the toxicity of the compounds of this invention were determined by the test methods described below, and the results of these tests for a few representative species of the genus are shown in Tables I and II, where A = (E)-2-[(amino)phenylmethylene]-benzo[b]thiophen-3(2H)-one, B = (E)-2-[(methylamino)phenylmethylene]-benzo[b]thiophen-3(2H)-one, C = (E)-2-[(amino)-(2-chloro-phenyl)methylene]-benzo[b]thiophen-3(2H)-one, D = (E)-2-{[(2-hydroxy-ethyl)amino]phenylmethylene}benzo[b]thiophen-3(2H)-one, E = (E)-2-[(amino)-(2-methyl-phenyl)methylene]-benzo[b]-thiophen-3(2H)-one, and F = (E)-2-[(ethylamino)phenylmethylene]-benzo[b]thiophen-3(2H)-one-

1. Anticonvulsant activity in mice

The anticonvulsant activity was tested as the inhibition of the tonic extensor spasm of the rear legs of male mice under maximum electric shock.

Method

The test animals were male SPF mice (Chbb:NMRI) weighing 20 to 26 g which, up to one hour before oral administration of the test compound, had access to standard feed and drinking water.

The test procedure was based on that of SWINYARD, BROWN and GOODMAN (J. Pharmacol. Exp. Ther. 106, 319 [1952]). The electrical shock equipment was manufactured in accordance with information provided by WOODBURY and DAVENPORT (Arch. int. Pharmacodyn. 92, 97 [1952]). The electrical stimuli were applied to the heads of the animals above the eyes using chamois-covered steel ball electrodes moistened with a 0.9% NaCl solution. The stimulus lasted 0.2 sec. using alternating current of 50 Hz and 50 mA. There was a chronic and then a tonic stretching spasm of the extremities in the case of all the controls. The tonic stretching spasm does not occur in the case of animals protected by anticonvulsants.

The substance to be tested was suspended in a 1% tylose slurry and was perorally administered in a volume of 0.1 ml/10 gm mouse to 10 mice/dose. The animals were subjected to shock treatment 30, 140 and 300 minutes after administering the substance, and the $ED_{50}$ values were determined as the dosages sufficient to protect 50% of the animals against the tonic stretching spasm of the rear extremities, either graphically or by the method of LITCHFIELD and WILCOXON (J. Pharmacol. Exp. Ther. 96, 99 [1949]).

Results

TABLE I

| Compound | $ED_{50}$ mg/kg p.o. minutes | | |
|---|---|---|---|
| | 30 | 150 | 300 |
| A | 12.8 | 37 | 46 |
| B | 90 | 38 | 49 |
| C | 7.0 | 4.4 | 5.0 |
| D | 33 | 41 | 42.5 |
| E | 22.8 | 13.3 | 15.7 |
| F | 22.5 | 54.6 | 79 |

2. Acute toxicity

The orienting acute toxicity of the compounds was determined after administering a dose to groups of 6 or 10 mice each with body weights between 10 and 26 gm (observation period: 7 days).

| Compound | Orienting acute toxicity | $(LD_{50})$ |
|---|---|---|
| A | 2,400 mg/kg p.o. | |
| B | > 1,000 mg/kg p.o. | |
| C | 500 to 1,000 mg/kg p.o. | |
| D | > 1,000 mg/kg p.o. | |
| E | > 1,000 mg/kg p.o. | |
| F | > 1,000 mg/kg p.o. | |

For pharmaceutical purposes the compounds of the present invention are administered to warm-blooded animals perorally, parenterally or rectally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective dosage unit of the compounds according to the present invention is from 0.83 to 5.0 mgm/kg body weight, preferably 1.66 to 2.50 mgm/kg body weight. The daily dose is 1.5 to 15.0 mgm/kg, preferably 2.50 to 7.5 mgm/kg.

The following examples illustrate a few pharmaceutical dosage unit compositions comprising a compound of the present invention as an active ingredient and represent the best modes contemplated of practicing the invention. The parts are parts by weight unless otherwise specified.

EXAMPLE 69

Tablets

The tablet composition is compounded from the following ingredients:

| | |
|---|---|
| (E)-2-[(Amino)phenylmethylene]-benzo[b]thiophen-3(2H)-one | 50 parts |
| Lactose | 148 parts |
| Potato starch | 60 parts |
| Magnesium stearate | 2 parts |
| Total | 260 parts |

Preparation:

The active ingredient and the lactose are stirred into an aqueous 10% solution of the potato starch, the mixture is granulated by passing it through a 1.5 mm-mesh screen, and the granulate is dried and again passed through the screen. The dry granulate is admixed with the magnesium stearate, and the composition is compressed into 260 mgm-tablets. Each tablet is an oral dosage unit composition containing 50 mgm of the active ingredient.

EXAMPLE 70

Coated tablets

The composition of the preceding example is compressed into 260 mgm-tablet cores which are subsequently coated with a thin shell consisting essentially of a mixture of sugar and talcum. The coated tablets are finally polished with beeswax.

Any one of the other compounds embraced by formula I may be substituted for the particular active ingredient in Examples 69 and 70. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

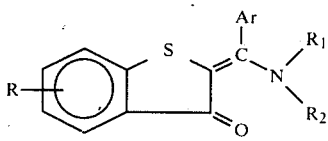

wherein

Ar is phenyl; mono- or di-substituted phenyl, where the substituents are one to two halogens, one to two alkyls of 1 to 3 carbon atoms, or one amino, nitro, cyano or trifluoromethyl; or pyridinyl;

R is hydrogen, chlorine, methyl or methoxy;

$R_1$ is hydrogen or methyl;

$R_2$ is hydrogen, alkyl of 1 to 6 carbon atoms, alkenyl of 2 to 6 carbon atoms, alkynyl of 2 to 6 carbon atoms, cycloalkyl of 3 to 8 carbon atoms, methyl-(cycloalkyl of 3 to 8 carbon atoms) or —A—$R_4$, wherein A is alkylene of 2 to 3 carbon atoms, and $R_4$ is hydroxyl, methylamino, dimethylamino, N-methyl-ethylamino, diethylamino, pyrrolidino, piperidino, hexamethyleneimino, morpholino or 4-methyl-1-piperazinyl; or $R_1$ and $R_2$, together with each other and the nitrogen atom to which they are attached, are pyrrolidino, piperidino, morpholino, N-methyl-piperazino, thiomorpholino, thiomorpholino-S-oxide or hexamethyleneimino.

2. A compound of claim 1, where

Ar is unsubstituted or o-substituted phenyl, where the substituent is fluorine, chlorine, bromine, methyl or ethyl;

R is hydrogen;

$R_1$ is hydrogen or methyl; and $R_2$ is hydrogen, methyl, ethyl, β-hydroxy-ethyl or β-dimethylamino-ethyl.

3. The compound of claim 1 which is (E)-2-[(amino)-phenylmethylene]-benzo[b]thiophen-3(2H)-one.

4. The compound of claim 1 which is (E)-2-[(methylamino)phenylmethylene]-benzo[b]thiophen-3(2H)-one.

5. The compound of claim 1 which is (E)-2-[(dimethylamino)phenylmethylene]-benzo[b]thiophen-3(2H)-one.

6. The compound of claim 1 which is (E)-2-[(amino)-(2-fluorophenyl)methylene]-benzo[b]thiophen-3(2H)-one.

7. The compound of claim 1 which is (E)-2-[(amino)-(2-chlorophenyl)methylene]-benzo[b]thiophen-3(2H)-one.

8. The compound of claim 1 which is (E)-2-{[[2-(dimethylamino)ethyl]amino]phenylmethylene}-benzo[b]thiophen-2(2H)-one.

9. The compound of claim 1 which is (E)-2-{[(2-hydroxyethyl)amino]phenylmethylene}-benzo[b]thiophen-3(2H)-one.

10. The compound of claim 1 which is (E)-2-[(amino)-(2-methylphenyl)methylene]-benzo[b]thiophen-3(2H)-one.

11. The compound of claim 1 which is (E)-2-[(ethylamino)phenylmethylene]-benzo[b]thiophen-3(2H)-one.

12. An anticonvulsant pharmaceutical dosage unit composition consisting essentially of an inert pharmaceutical carrier and an effective anticonvulsant amount of a compound of claim 1.

13. The method of preventing or relieving convulsions in a warm-blooded animal in need thereof, which comprises perorally, parenterally or rectally administering to said animal an effective anticonvulsant amount of a compound of claim 1.

* * * * *

UNITED STATES PATENT AND TRADEMARK OFFICE
CERTIFICATE OF CORRECTION

PATENT NO. : 4,288,437
DATED : September 8, 1981
INVENTOR(S) : WOLFHARD ENGEL ET AL.

It is certified that error appears in the above—identified patent and that said Letters Patent is hereby corrected as shown below:

Column 1, line 29: "methyl(-" should read -- methyl- --.

line 30: "cycloalkyl" should read -- (cycloalkyl --.

Column 4, line 2; Column 4, line 46: "B" should read -- $B^{\ominus}$ --.

Column 7, line 52: "formula V" should read -- formula IV --.

Column 8, line 26: "methylbenzyl" should read -- methylbenzoyl --

Column 9, line 67; Column 10, line 37: "dichloroe-" should read -- dichloro- --.

Column 9, line 68; Column 10, line 38: "thane" should read -- ethane --.

Column 10, line 18: After "followed" insert -- by filtering --.

Column 15, line 40: "petroluem" should read -- petroleum --.

Column 16, line 19: "2-(ethyl-benzoyl)" should read -- 2-(2-ethyl-benzoyl) --.

Column 19, lines 34 and 49: [(methox-" should read -- [(methoxy)- --.

UNITED STATES PATENT AND TRADEMARK OFFICE
CERTIFICATE OF CORRECTION

PATENT NO. : 4,288,437
DATED : September 8, 1981
INVENTOR(S) : WOLFHARD ENGEL ET AL.

It is certified that error appears in the above—identified patent and that said Letters Patent is hereby corrected as shown below:

Column 19, lines 35 and 50: Delete "y)".

Column 20, line 49: "-CH-" should read -- $-CH_2O-$ --.

line 50: Delete "$_2O-$"

Column 24, line 15: "[(hydrox-" should read -- [(hydroxy- --.

line 16: "yamino" should read -- amino --.

Column 31, line 20: "wherein" should read -- where --.

Signed and Sealed this

Twenty-third Day of March 1982

[SEAL]

Attest:

GERALD J. MOSSINGHOFF

Attesting Officer    Commissioner of Patents and Trademarks